(12) United States Patent
Johansson et al.

(10) Patent No.: US 7,935,681 B2
(45) Date of Patent: May 3, 2011

(54) ANTIVIRAL NUCLEOSIDES

(75) Inventors: Nils-Gunnar Johansson, Huddinge (SE); Genaidy Kalyanov, Huddinge (SE); Joseph Armstrong Martin, Hertfordshire (GB); David Bernard Smith, San Mateo, CA (US); Anna Winqvist, Huddinge (SE)

(73) Assignee: Medivir AB, Huddinge (SE)

(*) Notice: Subject to any disclaimer, the term of this patent is extended or adjusted under 35 U.S.C. 154(b) by 0 days.

(21) Appl. No.: 12/890,538

(22) Filed: Sep. 24, 2010

(65) Prior Publication Data
US 2011/0015148 A1    Jan. 20, 2011

Related U.S. Application Data

(63) Continuation of application No. 12/690,842, filed on Jan. 20, 2010, now Pat. No. 7,825,239, which is a continuation of application No. 11/973,681, filed on Oct. 10, 2007, now Pat. No. 7,666,856.

(60) Provisional application No. 60/850,926, filed on Oct. 10, 2006.

(51) Int. Cl.
A01N 43/04     (2006.01)
A61K 31/70     (2006.01)
C07H 19/00     (2006.01)

(52) U.S. Cl. ............. 514/51; 514/43; 514/49; 536/26.1; 536/28.1; 536/28.4; 536/28.5; 536/28.51

(58) Field of Classification Search ................... None
See application file for complete search history.

(56) References Cited

U.S. PATENT DOCUMENTS

| | | | |
|---|---|---|---|
| 5,034,518 A | 7/1991 | Montgomery | |
| 5,246,924 A | 9/1993 | Fox | |
| 5,587,362 A | 12/1996 | Chu | |
| 6,348,587 B1 | 2/2002 | Schinazi | |
| 6,784,166 B2 | 8/2004 | Devos | |
| 6,846,810 B2 | 1/2005 | Martin | |
| 6,864,244 B2 | 3/2005 | Connolly | |
| 7,456,155 B2 | 11/2008 | Sommadossi | |
| 7,666,856 B2 * | 2/2010 | Johansson et al. | 514/51 |
| 7,825,239 B2 * | 11/2010 | Kalyanov et al. | 536/28.53 |
| 2004/0259934 A1 | 12/2004 | Olsen | |
| 2005/0038240 A1 * | 2/2005 | Connolly et al. | 536/28.51 |

FOREIGN PATENT DOCUMENTS

| | | |
|---|---|---|
| EP | 292023 | 11/1988 |
| EP | 352248 | 1/1990 |
| EP | 357571 | 7/1990 |
| EP | 547008 | 6/1993 |
| WO | WO 88/08001 | 10/1988 |
| WO | WO 00/69876 | 11/2000 |
| WO | WO 00/69877 | 11/2000 |
| WO | WO 01/32153 | 5/2001 |
| WO | WO 01/90121 | 11/2001 |
| WO | WO 01/92282 | 12/2001 |
| WO | WO 02/18404 | 3/2002 |
| WO | WO 02/005787 | 7/2002 |
| WO | WO 02/057425 | 7/2002 |
| WO | WO 02/100415 | 12/2002 |
| WO | WO 03/026589 | 4/2003 |
| WO | WO 03/026675 | 4/2003 |
| WO | WO 03/039523 | 5/2003 |
| WO | WO 03/053349 | 7/2003 |
| WO | WO 2004/002422 | 1/2004 |
| WO | WO 2004/002999 | 1/2004 |
| WO | WO 2004/003000 | 1/2004 |
| WO | WO 2004/037855 | 5/2004 |
| WO | WO 2004/046159 | 6/2004 |
| WO | WO 2004/046331 | 6/2004 |
| WO | WO 2005/010029 | 2/2005 |
| WO | WO 2005/028501 | 3/2005 |
| WO | WO 2005/073195 | 8/2005 |
| WO | WO 2005/073216 | 8/2005 |
| WO | WO 2006/021341 | 3/2006 |

OTHER PUBLICATIONS

Carroll, et al, J Biol Chem (2003), 278(14), p. 11979-11984.
Jin, et al, Arch Pharm Res, (1995), 18(5), p. 364-365.
Jeon, et al, Tetrahedron, (1996), 52(39), p. 12643-12650.
Waga, et al, Nucleosides & Nucleotides, (1996), 15(1-3), p. 287-304.
Kitano, et al, Tetrahedron, (1997), 53(39), p. 13315-13322.
Maag, et al, J Med Chem, (1992), 35, p. 1440-1451.
Kohgo, et al, Biosci Biotechnol Biochem, (1999), 63(6), p. 1146-1149.
Kohgo, et al, Nucleic Acid Symposium Series, (1999), 42, p. 127-128.
Kodama, et al, Antimicrob Ag Chemother, (2001), 45(5), p. 1539-1546.
Ohrui, et al, J Med Chem, (2000), 43, p. 4516-4625.
Wu, et al, Curr Drug Targ Inf Dis, (2003), 3(3), p. 207-219.
Yamaguchi, et al, Nucleosides & Nucleotides, (1997), 16(7-9), p. 1347-1350.
Sugimoto, et al, Biorg Med Chem Lett, (1999), 9, p. 385-388.
Yang, et al, Tetrahedron Lett, (1992), 33(1), p. 37-40.
Yang, et al, Tetrahedron Lett, (1992), 33(1), p. 41-44.
Borthwick, et al, J Med Chem, (1990), 33, p. 179-186.
Cicero, et al, Biorg Med Chem Lett, (1994), 4(7), p. 861-866.
Murakimi, et al, Antimicrob Ag Chemother, (2007), 51(2), p. 503-509.
Klump, et al, J Biol Chem, (2006), 281(7), p. 3793-3799.
Klump, et al, J Biol Chem, (2008), 283(4), p. 2167-2175.
Smith, et al, Biorg Med Chem Lett, (2007), 17, p. 2570-2576.

* cited by examiner

Primary Examiner — Traviss C McIntosh, III
(74) Attorney, Agent, or Firm — Birch, Stewart, Kolasch and Birch, LLP

(57) ABSTRACT

4-Amino-1-((2R,3S,4S,5R)-5-azido-4-hydroxy-5-hydroxymethyl-3-methyl-tetrahydro-furan-2-yl)-1H-pyrimidin-2-one (22) and prodrugs thereof are hepatitis C (HCV) polymerase inhibitors. Also disclosed are compositions and methods for inhibiting HCV and treating HCV-mediated diseases, processes for making the compounds and synthetic intermediates employed in the process.

4 Claims, No Drawings

ANTIVIRAL NUCLEOSIDES

CROSS REFERENCE TO PRIOR APPLICATIONS

This application is a Divisional of U.S. Utility application Ser. No. 12/690,842 filed on Jan. 20, 2010, now U.S. Pat. No. 7,825,239, which is a Continuation of U.S. Utility application Ser. No. 11/973,681 filed on Oct. 10, 2007, now U.S. Pat. No. 7,666,856 which claims priority to U.S. Provisional Application No. 60/850,926, filed on Oct. 10, 2006, all of which are hereby incorporated by reference in their entirety.

FIELD OF THE INVENTION

The present invention provides nucleoside compounds and certain derivatives thereof which are inhibitors of RNA-dependent RNA viral polymerase. These compounds are inhibitors of RNA-dependent RNA viral replication and are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

The invention relates to nucleoside inhibitors of HCV replicon RNA replication. In particular, the invention is concerned with the use of pyrimidine nucleoside compounds as inhibitors of subgenomic HCV RNA replication and pharmaceutical compositions containing such compounds.

Hepatitis C virus is the leading cause of chronic liver disease throughout the world. (Boyer, N. et al. *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., *Flaviviridae: The viruses and their replication, in: Fields Virology*, Editors: Fields, B. N., Knipe, D. M., and Howley, P. M., Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a 5'-untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forms and J. Bukh, *Clinics in Liver Disease* 1999 3:693-716; J. Bukh et al., *Semin. Liv. Dis.* 1995 15:41-63). Unfortunately Type 1 infections are more resistant to therapy than either type 2 or 3 genotypes (N. N. Zein, *Clin. Microbiol. Rev.,* 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown. It is believed that most of the non-structural proteins encoded by the HCV RNA genome are involved in RNA replication.

Currently there are a limited number of approved therapies available for the treatment of HCV infection. New and existing therapeutic approaches to treating HCV and inhibition of HCV NS5B polymerase have been reviewed: R. G. Gish, *Sem. Liver. Dis.,* 1999 19:5; Di Besceglie, A. M. and Bacon, B. R., *Scientific American*, October: 1999 80-85; G. Lake-Bakaar, Current and Future Therapy for Chronic Hepatitis C Virus Liver Disease, *Curr. Drug Targ. Infect Dis.* 2003 3(3): 247-253; P. Hoffmann et al., Recent patents on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. investing. Drugs* 2003 12(8):1269-1280; S.-L. Tan et al., Hepatitis C Therapeutics: Current Status and Emerging Strategies, *Nature Rev. Drug Discov.* 2002 1:867-881.

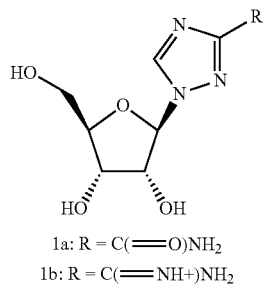

1a: R = C(═O)NH$_2$
1b: R = C(═NH+)NH$_2$

Ribavirin (1a; 1-((2R,3R,4S,5R)-3,4-Dihydroxy-5-hydroxymethyl-tetrahydro-furan-2-yl)-1H-[1,2,4]triazole-3-carboxylic acid amide; Virazole) is a synthetic, non-interferon-inducing, broad spectrum antiviral nucleoside analog. Ribavirin has in vitro activity against several DNA and RNA viruses including Flaviviridae (Gary L. Davis, *Gastroenterology* 2000 118:S104-S114). In monotherapy ribavirin reduces serum amino transferase levels to normal in 40% of patients, but it does not lower serum levels of HCV-RNA. Ribavirin also exhibits significant toxicity and is known to induce anemia. Viramidine 1b is a prodrug converted to 1a in hepatocytes.

Interferons (IFNs) have been available for the treatment of chronic hepatitis for nearly a decade. IFNs are glycoproteins produced by immune cells in response to viral infection. Two distinct types of interferons are recognized: Type 1 includes several interferon as and one interferon β, type 2 includes interferon y. Type 1 interferons are produced mainly by infected cells and protects neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (L.-B. Davis, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release*, 2001 72:217-224).

Combination therapy of HCV with ribavirin and interferon-α currently represent the optimal therapy. Combining ribavirin and PEG-IFN (infra) results in a sustained viral response in 54-56% of patients. The SVR approaches 80% for type 2 and 3 HCV. (Walker, supra) Unfortunately, the combination also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome. This enzyme has elicited significant interest among medicinal chemists. Both nucleoside and non-nucleoside inhibitors of NS5B are known.

Nucleoside inhibitors can act either as a chain terminator or as a competitive inhibitor which interferes with nucleotide binding to the polymerase. To function as a chain terminator the nucleoside analog must be taken up be the cell and converted in vivo to a triphosphate to compete for the polymerase nucleotide binding site. This conversion to the triphosphate is commonly mediated by cellular kinases which imparts additional structural requirements on a potential nucleoside polymerase inhibitor. In addition this limits the direct evaluation of nucleosides as inhibitors of HCV replication to cell-based assays capable of in situ phosphorylation.

In WO 01 90121 published Nov. 29, 2001, J.-P. Sommadossi and P. Lacolla disclose and exemplify the anti-HCV polymerase activity of 1'-alkyl- and 2'-alkyl nucleosides of formulae 2 and 3. In WO 01/92282, published Dec. 6, 2001, J.-P. Sommadossi and P. Lacolla disclose and exemplify treating Flaviviruses and Pestiviruses with 1'-alkyl- and 2'-alkyl nucleosides of formulae 2 and 3. In WO 03/026675 and WO03/026589, both published Apr. 3, 2003, G. Gosselin et al. discloses 4'-alkyl nucleosides 4 and methods of using 4'-alkyl nucleosides for treating Flaviviruses and Pestiviruses. In WO2004003000 and WO2004002999, both published Jan. 8, 2004, J.-P. Sommadossi et al. disclose prodrugs of 1'-, 2'-, 3'- and 4'-substituted β-D and β-L nucleosides. In WO04/002422 published Jan. 8, 2004 J.-P. Sommadossi et al. disclose the 3'-O-L-valine ester of 2'-C-methyl-ribofuranosyl cytidine and its use in the treatment of HCV.

Idenix has reported clinical trials for a related compound NM283 which is the valine ester 5 of the cytidine analog 2 (B=cytosine). Further, Idenix Pharmaceuticals, Ltd. also discloses in WO 04/046331 Flaviviridae mutations caused by biologically active 2'-branched β-D or β-L nucleosides or a pharmaceutically acceptable salt or prodrug thereof.

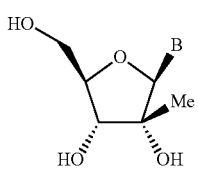

2

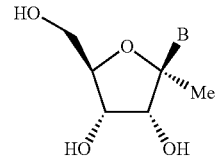

3

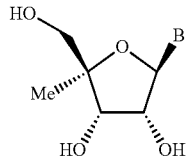

4

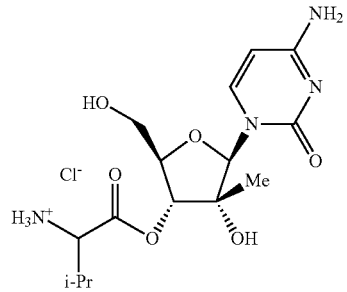

5

B = adenine, thymidine, uracil, cytidine, guanine and hypoxanthine

In WO02/057425 published Jul. 25, 2002, S. S. Carroll et al. disclose nucleoside inhibitors of RNA-dependent RNA polymerase wherein the carbohydrate subunit is chemically modified. In WO02/05787 published Jul. 25, 2002, S. S. Carroll et al. disclose related 2α-methyl and 2β-methylribose derivatives wherein the base is an optionally substituted 7H-pyrrolo[2,3-d]pyrimidine radical 6. The same application discloses one example of a 3β-methyl nucleoside. S. S. Carroll et al. (*J. Biol. Chem.* 2003 278(14):11979-11984) disclose inhibition of HCV polymerase by 2'-O-methylcytidine (6a). In U.S. Publication No. 2004/0259934 published Dec. 23, 2004, D. B. Olsen et al. disclose methods of inhibiting Coronaviridae viral replication and treating Coronaviridae viral infection with nucleoside compounds.

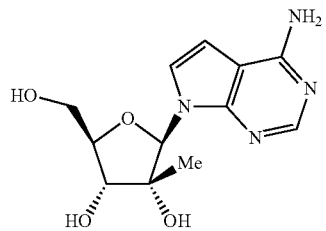

6

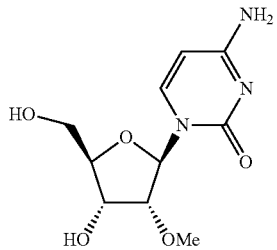

6a

In WO02/100415 published Dec. 19, 2002 (US 2003/0236216 A1), R. R. Devos et al. disclose 4I-substituted nucleoside compounds that exhibit HCV activity. Four compounds explicitly identified include the 4'-azido compound, 7a, the 4'-ethynyl compound 7b, the 4I-ethoxy compound 7c and the 4'-acetyl compound 7d. Modifications to the ribose moiety exemplified include the 2'-deoxy 8a derivative, 3'-deoxy derivative 8b, the 3'-methoxy derivative 8e, the 3'-fluoro derivative 8c and the 2',2'-difluoro derivative 8d. In WO2004/046159 published Jun. 3, 2004 (US 2004121980), J. A. Martin et al. disclose prodrugs of 7a useful for treating HCV-mediated diseases. Both

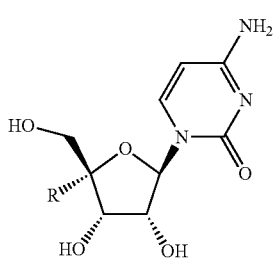

7a: R = N₃
7b: R = ethynyl
7c: R = OEt
7d: R = C(═O)Me

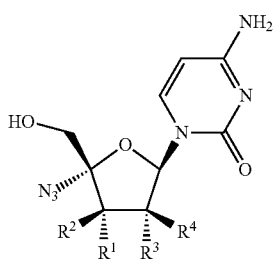

8a: R¹ = OH, R² = R³ = R⁴ = H
8b: R³ = OH, R¹ = R² = R⁴ = H
8c: R³ = OH, R² = F, R¹ = R⁴ = H
8d: R¹ = R² = H, R³ = R⁴ = F
8e: R¹ = OMe, R³ = OH, R² = R⁴ = H

US applications are hereby incorporated by reference in their entirety. U.S. application Ser. No. 10/167,106 filed Jun. 11, 2002 entitled "4'-Substituted Nucleoside Derivatives as Inhibitors of HCV RNA Replication", and U.S. application Ser. No. 10/717,260 file Nov. 19, 2003 disclose compounds related to the present invention. Both applications are incorporated herein in their entirety by reference.

Y.-H. Yun et al. (*Arch. Pharm. Res.* 1985 18(5):364-35) disclose the synthesis and antiviral activity of 4'-azido-2'-deoxy-2'-fluoro-arabinofuranosyl nucleosides (9: R═H, Me and Cl).

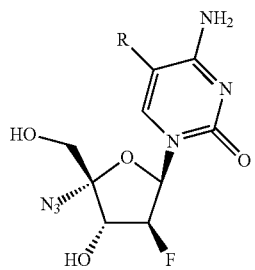

9

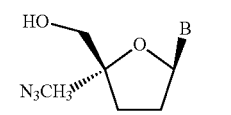

10

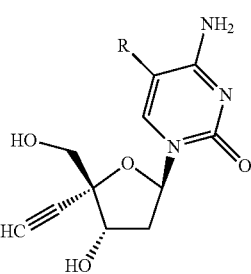

11

B = adenine, uracil, thymine

G. S. Jeon and V. Nair (*Tetrahedron* 1996 52(39):12643-50) disclose the synthesis 4'-azidomethyl-2',3'-deoxyribonucleosides 10 (B=adenine, thymine and uracil) as HIV reverse transcriptase inhibitors.

Several computational studies of 4'-azidonucleosides have been reported: D, Galisteo et al., *J. Mol. Struct.* 1996 384(1):25-33; J. Pepe et al., *Eur. J. Med. Chem.* 1996 32(10):775-786; E. Estrada et al., In silico studies toward the discovery of New Anti HIV Nucleoside, *J. Chem. Info. Comp. Sci.* 2002 42(5): 1194-1203.

I. Sugimoto et al. disclosed the synthesis and the HIV and H. simplex bioassay of 4'-ethynyl-2'-deoxycytidine (11) and other two-carbon substituents at the 4'-position (Nucleosides and Nucleotides. 183. Synthesis of 4' β-Branched Thymidines as a New Type of Antiviral Agent, *Bioorg. Med. Chem. Lett.* 1999 9:385-88). T. Wada et al. (*Nucleosides & Nucleotides* 1996 15(1-3):287-304) disclose the synthesis and anti-HIV activity of 4'-C-methyl nucleosides.

In WO 01/32153 published May 10, 2001, R. Storer discloses methods of treating or preventing Flaviviridae viral infection by administering dioxolane analogs of nucleosides.

In WO02/18404 published Mar. 7, 2002, R. Devos et al. disclose novel and known purine and pyrimidine nucleoside derivatives and their use as inhibitors of subgenomic HCV replication and pharmaceutical compositions containing said nucleoside derivatives. The compounds disclosed consist of nucleosides with substituted purine and pyrimidine bases.

EPA Publication No. 0 352 248 discloses a broad genus of L-ribofuranosyl purine nucleosides for the treatment of HIV, herpes, and hepatitis. A similar specification is found in WO 88/09001, filed by Aktiebolaget Astra.

K. Kitano et al. (*Tetrahedron* 1997 53(39):13315-13322) disclose the synthesis 4'-fluoromethyl 2-deoxy-D-erythro-, ribo- and arabino-pentofuranosyl cytosines and anti-neoplastic activity.

Non-nucleoside allosteric inhibitors of HIV reverse transcriptase have proven effective therapeutics alone and in combination with nucleoside inhibitors and with protease inhibitors. Several classes of non-nucleoside HCV NS5B inhibitors have been described and are currently at various stages of development including: benzimidazoles, (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1); indoles, (P. L. Beaulieu et al. WO 03/0010141 A2); benzothiadiazines, e.g., 1, (D. Dhanak et al. WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al. WO2004052313, filed Dec. 13, 2003; D. M. Fitch et al., WO2004058150, filed Dec. 11, 2003; D. K. Hutchinson et al. WO2005019191, filed Aug. 19, 2004; J. K. Pratt et al. WO 2004/041818 A1, filed

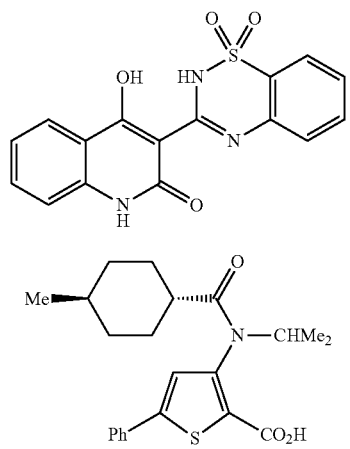

1

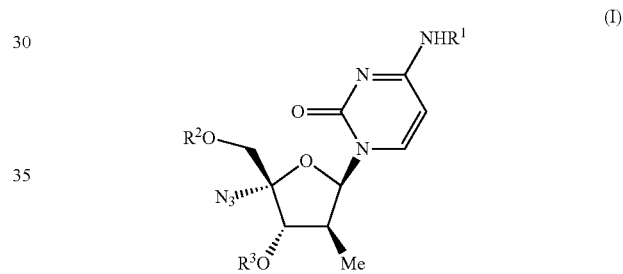

2

Oct. 31, 2003); thiophenes, e.g., 2, (C. K. Chan et al. WO 02/100851 A2); benzothiophenes (D. C. Young and T. R. Bailey WO 00/18231); β-ketopyruvates (S. Attamura et al. U.S. Pat. No. 6,492,423 B1, A. Attamura et al. WO 00/06529); pyrimidines (C. Gardelli et al. WO 02/06246 A1); pyrimidinediones (T. R. Bailey and D. C. Young WO 00/13708); triazines (K.-H. Chung et al. WO 02/079187 A1); rhodanine derivatives (T. R. Bailey and D. C. Young WO 00/10573, J. C. Jean et al. WO 01/77091 A2); 2,4-dioxopyrans (R. A. Love et al. EP 256628 A2); phenylalanine derivatives (M. Wang et al. *J. Biol. Chem.* 2003 278:2489-2495). Thiazines that inhibit HCV NS5B have been disclosed by J. F. Blake et al. in U.S. Pub. No. 20060040927 filed Aug. 22, 2005.

Inhibitors of HCV protease required for viral replication also have been disclosed (F. McPhee et al., *Drugs of the Future* 2003 28(5):465-488; Y. S. Tsantrizos et al., *Angew. Chem. Int. Ed. Eng.* 2003 42(12):1356-1360). A nucleoside compound of the present invention may be used in combination with these and other polymerase and protease inhibitors.

The results of these efforts have been reviewed (J. Z. Chen and Z. Hong, Targeting NS5B RNA-Dependent RNA Polymerase for Anti-HCV Chemotherapy, Curr. Drug Targ. *Inf. Dis.* 2003 3(3):207-219). The non-nucleoside inhibitors are not related to the present invention.

The object of the present invention is to provide new nucleoside compounds, methods and compositions for the treatment of a host infected with hepatitis C virus.

SUMMARY OF THE INVENTION

There is currently no preventive treatment of Hepatitis C virus (HCV) and currently approved therapies, which exist only against HCV, are limited. Design and development of new pharmaceutical compounds is essential.

Surprisingly, 2'-deoxy-2-β-methyl-4'-azido-cytidine or esters thereof are useful treating HCV and exhibit lower toxicity following administration to a host. The present invention also provides for pharmaceutical compositions of the compound and at least one pharmaceutically acceptable carrier, excipient or diluent.

Combination therapy has proven useful for the treatment of viral disease and new compounds synergistic with other approved and investigational HCV therapeutics and the present invention provides for treatment of HCV with nucleosides of the general formula disclosed above, or a pharmaceutically acceptable salt, in combination or alternation with one or more other effective antiviral agent(s) or immunomodulators, optionally including at least one pharmaceutically acceptable carrier, excipient or diluent.

(I)

$$\text{structure of formula I}$$

The present invention provides a nucleoside according to formula I, or a pharmaceutically acceptable salt thereof, and the use of such compounds for the treatment of a host infected with HCV wherein:

$R^1$, $R^2$ and $R^3$ are independently selected from the group consisting of hydrogen, $COR^4$, $C(=O)OR^4$ and $C(=O)CHR^5NHR^6$;

$R^4$ is independently selected from the group consisting of (a) $C_{1-18}$ unbranched or branched alkyl, (b) $C_{1-18}$ haloalkyl, (c) $C_{3-8}$ cycloalkyl, (d) $C_{1-10}$ heteroalkyl and (e) phenyl said phenyl optionally substituted with one to three groups independently selected from $C_{1-3}$ alkyl, $C_{1-3}$ alkoxy, halogen, cyano or nitro;

$R^5$ is hydrogen, $C_{1-10}$ alkyl, phenyl or $C_{1-3}$ phenylalkyl said phenyl optionally substituted with one to three groups independently selected from the group consisting of halogen, hydroxy, $C_{1-3}$ alkoxy, $C_{1-3}$ alkyl, cyano and nitro;

$R^6$ is hydrogen or $C_{1-6}$ alkoxy; or, acid addition salts thereof.

The present invention also provides for the use according to formula I, or a pharmaceutically acceptable salt, optionally in combination other effective antiviral agent(s) and optionally including at least one pharmaceutically acceptable carrier, excipient or diluent for the treatment of HCV infection in the manufacture of a medicament for the treatment or prophylaxis HCV in a host.

Without wishing to be bound by theory, it is believed that the compounds of the invention are serially phosphorylated in human cells by kinases to the 5'-O-monophosphate, 5'-O-diphosphate and ultimately the 5'-O-triphosphate which is the antivirally active metabolite. A further aspect of the invention thus provides these 5'-O phosphorylated species, ie compounds of the formula I wherein $R^1$ and $R^3$ are H and $R^2$ is a monophosphate, diphosphate or triphosphate ester.

The antiviral activity of a nucleoside inhibitor is typically the combined outcome of uptake of the nucleoside into host cells, conversion of the nucleoside to the active triphosphate, intracellular stability of the triphosphate, and the ability of the triphosphate to interfere with the RNA synthesis activity of the viral polymerase. As presented in the biological examples below, the compounds of the invention are readily phosphorylated in vivo to the active triphosphate and have a long intracellular triphosphate half life, thereby allowing sustained and high concentrations of the antivirally active species.

DETAILED DESCRIPTION OF THE INVENTION

In one embodiment of the present invention there is provided a compound according to formula I wherein $R^1$, $R^2$, $R^3$, $R^4$, $R^5$ and $R^6$ are as defined herein above; or a pharmaceutically acceptable salt thereof. The phrase "as defined herein above" refers to the broadest definition for each group as provided in the Summary of the Invention. In other embodiments provided below, substituents present in each embodiment which are not explicitly defined retain the broadest definition provided in the Summary of the Invention.

In another embodiment of the present invention there is provided a compound according to formula I wherein $R^1$, $R^2$, $R^3$ are hydrogen; or a pharmaceutically acceptable salt thereof.

In another embodiment, there is provided a compound according to formula I wherein $R^1$ and $R^3$ are H and $R^2$ is a monophosphate, diphosphate or triphosphate ester.

In yet another embodiment of the present invention there is provided a compound according to formula I wherein $R^1$, $R^2$, $R^3$ each are independently hydrogen, $COR^4$ or $C(=O)OR^4$ and $R^4$ is as described hereinabove; or a pharmaceutically acceptable salt thereof.

In still another embodiment of the present invention there is provided a compound according to formula I wherein $R^1$, $R^2$, $R^3$ each are independently hydrogen, $COR^4$ or $C(=O)OR^4$ and $R^4$ is unbranched or branched $C_{1-10}$ alkyl, such as lower alkyl, especially methyl, ethyl, i-propyl or t-butyl; or a pharmaceutically acceptable salt thereof.

In still another embodiment of the present invention there is provided a compound according to formula I wherein $R^1$ is hydrogen; $R^2$ and $R^3$ are $COR^4$, or a pharmaceutically acceptable salt thereof.

In still another embodiment of the present invention there is provided a compound according to formula I wherein $R^1$ is hydrogen; $R^2$ and $R^3$ are $COR^4$, and $R^4$ is unbranched or branched $C_{1-10}$ alkyl, such as lower alkyl, especially methyl, ethyl, i-propyl or t-butyl; or a pharmaceutically acceptable salt thereof. Where a compound to comprises two $R^4$ moieties they are typically the same, for synthetic convenience.

In still another embodiment of the present invention there is provided a compound according to formula I wherein $R^1$ and $R^3$ are hydrogen; $R^2$ is $COR^4$, $C(=O)OR^4$ or $COCH(R^5)NHR^6$; and $R^4$, $R^5$ and $R^6$ are as defined herein above; or a pharmaceutically acceptable salt thereof.

In still another embodiment of the present invention there is provided a compound according to formula I wherein $R^1$ and $R^2$ are hydrogen; $R^3$ is $COR^4$, $C(=O)OR^4$ or $COCH(R^5)NHR^6$; and $R^4$, $R^5$ and $R^6$ are as defined herein above; or a pharmaceutically acceptable salt thereof.

In another embodiment of the present invention there is provided a compound according to formula I wherein $R^2$ is $COCH(R^5)NHR^6$, $R^5$ is iso-propyl, iso-butyl or sec-butyl and $R^6$ is hydrogen. In a preferred arrangement of this embodiment, the steric configuration of the $R^5$ group is (S), that is $R^2$ is an L-aliphatic amino acid residue. $R^1$ in this embodiment is typically H, whereas $R^3$ is H or $COCH(R^5)NHR^6$, $R^5$ is iso-propyl, iso-butyl or sec-butyl and $R^6$ is hydrogen. Where a compound has two such $COCH(R^5)NHR^6$ moieties they are typically the same amino acid for synthetic convenience.

In another embodiment of the present invention there is provided a compound according to formula I wherein $R^3$ is $COCH(R^5)NHR^6$, $R^5$ is iso-propyl, iso-butyl or sec-butyl and $R^6$ is hydrogen. In a preferred arrangement of this embodiment, the steric configuration of the $R^5$ group is (S), that is $R^3$ is an L-aliphatic amino acid residue. $R^1$ in this embodiment is typically H.

In yet another embodiment of the present invention there is provided a compound according to formula I wherein $R^1$ and $R^3$ are hydrogen; $R^2$ is $COR^4$; and $R^4$ is as defined herein above; or a pharmaceutically acceptable salt thereof.

In another embodiment of the present invention there is provided a compound according to formula I wherein $R^1$ and $R^3$ are hydrogen; $R^2$ is $COR^4$; and $R^4$ is $C_{1-10}$ unbranched or branched alkyl, such as lower alkyl, especially methyl, ethyl, i-propyl or t-butyl; or a pharmaceutically acceptable salt thereof.

In another embodiment of the present invention there is provided a method of treating a disease mediated by the Hepatitis C Virus (HCV) virus comprising administering to a mammal in need thereof, a therapeutically effective quantity of a compound according to formula I wherein $R^1$, $R^2$, $R^3$, $R^4$, $R^5$ and $R^6$ are as defined herein above; or a pharmaceutically acceptable salt thereof.

In another embodiment of the present invention there is provided a method of treating a disease mediated by the Hepatitis C Virus (HCV) virus comprising administering to a mammal in need thereof, a therapeutically effective quantity of a compound according to formula I wherein $R^1$, $R^2$ and $R^3$ are hydrogen; or a pharmaceutically acceptable salt thereof.

In another embodiment of the present invention there is provided a method of treating a disease mediated by the Hepatitis C Virus (HCV) virus comprising administering to a mammal in need thereof, a therapeutically effective quantity of a compound according to formula I wherein $R^1$ is hydrogen; $R^2$ and $R^3$ are each $COR^4$; $R^4$ is selected from the group consisting of $C_{1-10}$ unbranched or branched lower alkyl; or a pharmaceutically acceptable salt thereof.

In another embodiment of the present invention there is provided a method of treating a disease mediated by the Hepatitis C Virus (HCV) virus comprising administering to a mammal in need thereof, a therapeutically effective quantity of a compound according to formula I wherein $R^1$ and $R^3$ are hydrogen; $R^2$ is $COR^4$ or $COCH(R^5)NHR^6$; $R^4$ is selected from the group consisting of $C_{1-10}$ unbranched or branched lower alkyl; $R^5$ and $R^6$ are as defined herein above; or a pharmaceutically acceptable salt thereof.

In another embodiment of the present invention there is provided a method of treating a disease mediated by the Hepatitis C Virus (HCV) virus comprising administering to a mammal in need thereof, a dose of between 1 and 100 mg/kg of body weight of the patient per day of a compound according to formula I wherein $R^1$, $R^2$, $R^3$, $R^4$, $R^5$ and $R^6$ are as defined herein above, or a pharmaceutically acceptable salt thereof.

In another embodiment of the present invention there is provided a method of to treating a disease mediated by the Hepatitis C Virus (HCV) virus comprising co-administering to a mammal in need thereof, a therapeutically effective quantity of a compound according to formula I wherein $R^1$, $R^2$, $R^3$, $R^4$, $R^5$ and $R^6$ are as defined herein above, or a pharmaceutically acceptable salt thereof; and, at least one immune system modulator and/or at least one antiviral agent that inhibits replication of HCV.

In another embodiment of the present invention there is provided a method of treating a disease mediated by the Hepatitis C Virus (HCV) virus comprising co-administering to a mammal in need thereof, a therapeutically effective quantity of a compound according to formula I wherein $R^1$, $R^2$, $R^3$, $R^4$, $R^5$ and $R^6$ are as defined herein above, or a pharmaceutically acceptable salt thereof; and, at least one immune system modulator selected from interferon, interleukin, tumor necrosis factor or colony stimulating factor. One skilled in the medical art will be aware these immune system molecules may be in their naturally occurring form or they may be chemically derivatized to impart beneficial pharmacokinetic properties.

In another embodiment of the present invention there is provided a method of treating a disease mediated by the Hepatitis C Virus (HCV) virus comprising co-administering to a mammal in need thereof, a therapeutically effective quantity of a compound according to formula I wherein $R^1$, $R^2$, $R^3$, $R^4$, $R^5$ and $R^6$, or a pharmaceutically acceptable salt thereof, are as defined herein above; and an interferon or chemically derivatized interferon.

In another embodiment of the present invention there is provided a method of treating a disease mediated by the Hepatitis C Virus (HCV) virus comprising co-administering to a mammal in need thereof, a therapeutically effective quantity of a compound according to formula I wherein $R^1$, $R^2$, $R^3$, $R^4$, $R^5$ are as defined herein above, or a pharmaceutically acceptable salt thereof; and, at least one other antiviral agent.

In another embodiment of the present invention there is provided a method of treating a disease mediated by the Hepatitis C Virus (HCV) virus comprising co-administering to a mammal in need thereof, a therapeutically effective quantity of a compound according to formula I wherein $R^1$, $R^2$, $R^3$, $R^4$, $R^5$ are as defined herein above, or a pharmaceutically acceptable salt thereof; and, at least one other HCV protease inhibitor, another nucleoside HCV polymerase inhibitor, a non-nucleoside HCV polymerase inhibitor, an HCV helicase inhibitor, an HCV primase inhibitor or an HCV fusion inhibitor.

In one embodiment of the present invention there is provided a pharmaceutical composition comprising a therapeutically effective quantity of a compound according to formula I wherein $R^1$, $R^2$, $R^3$, $R^4$, $R^5$ and $R^6$ are as defined herein above; or a pharmaceutically acceptable salt thereof, admixed with at least one pharmaceutically acceptable carrier, diluent or excipient.

In another embodiment of the present invention there is provided a pharmaceutical composition comprising a 500-1500 mg compressed tablet containing 35-75 wt % of a compound according to formula I wherein $R^1$, $R^2$, $R^3$, $R^4$, $R^5$ and $R^6$ are as defined herein above; or a pharmaceutically acceptable salt thereof, and the remainder comprising at least one pharmaceutically acceptable carrier, diluent or excipient.

In another embodiment of the present invention there is provided a pharmaceutical composition comprising a 500-1500 mg compressed tablet containing 40-60 wt % of a compound according to formula I wherein $R^1$, $R^2$, $R^3$, $R^4$, $R^5$ and $R^6$ are as defined herein above; or a pharmaceutically acceptable salt thereof, and the remainder comprising at least one pharmaceutically acceptable carrier, diluent or excipient.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the first definition for each group as provided in the definition of formula I.

The terms "optional" or "optionally" as used herein means that a described event or circumstance may or may not occur, and that the description includes instances where said event or circumstance occurs and instances in which it does not. For example, to "optionally substituted phenyl" means that the phenyl may or may not be substituted and that the description includes both unsubstituted phenyl and phenyl wherein there is substitution.

Compounds of the present invention may have asymmetric centers located on the side chain of a carboxylic ester, amide or carbonate moiety that produce diastereomers when linked to the nucleoside. All stereoisomers of a side chain of compounds of the instant invention are contemplated, either in admixture or in pure or substantially pure form. The definition of the compounds according to the invention embraces all both isolated optical isomers enantiomers and their mixtures including the racemic form. The pure optical isomer can be prepared by stereospecific synthesis from □-D-ribose or the racemic form can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

The term "alkyl" as used herein denotes an unbranched or branched chain hydrocarbon residue containing 1 to 18 carbon atoms. The term "lower alkyl" denotes an unbranched or branched chain hydrocarbon residue containing 1 to 6 carbon atoms. Representative lower alkyl groups include methyl, ethyl, propyl, i-propyl, n-butyl, i-butyl, t-butyl or pentyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl.

The term "cycloalkylalkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cycloalkyl and R" is $C_{1-3}$ alkylene as defined herein.

The term "alkylene" as used herein denotes a divalent saturated linear hydrocarbon radical of 1 to 8 carbon atoms or a branched saturated divalent hydrocarbon radical of 3 to 8 carbon atoms, unless otherwise indicated. Examples of alkylene radicals include, but are not limited to, methylene, ethylene, propylene, 2-methyl-propylene, butylene, 2-ethylbutylene.

The term "alkenyl" as used herein denotes an unsubstituted [or substituted] hydrocarbon chain radical having from 2 to 18 carbon atoms, preferably from 2 to 4 carbon atoms, and having one or two olefinic double bonds, preferably one olefinic double bond. Examples are vinyl, 1-propenyl, 2-propenyl (allyl) or 2-butenyl (crotyl).

The term "alkynyl" as used herein denotes an unsubstituted hydrocarbon chain radical having from 2 to 18 carbon atoms, [preferably 2 to 4 carbon atoms], and having one or where possible two triple bonds [preferably one triple bond]. Examples are ethynyl, 1-propynyl, 2-propynyl, 1-butynyl, 2-butynyl or 3-butynyl.

The term "alkoxy" as used herein denotes an unsubstituted unbranched or branched chain alkyloxy group wherein the "alkyl" portion is as defined above such as methoxy, ethoxy, n-propyloxy, i-propyloxy, n-butyloxy, i-butyloxy, t-butyloxy, pentyloxy, hexyloxy, heptyloxy including their isomers. "Lower alkoxy" as used herein denotes an alkoxy group with a "lower alkyl" group as previously defined.

The term "alkylthio" or "thioalkyl" as used herein denotes an unbranched or branched chain (alkyl)S— group wherein the "alkyl" portion is as defined above. Examples are methylthio, ethylthio, n-propylthio, i-propylthio, n-butylthio, i-butylthio or t-butylthio.

The terms "alkylsulfinyl" and "arylsulfinyl" as used herein denotes a group of formula —S(=O)R wherein R is alkyl or aryl respectively and alkyl and aryl are as defined herein The terms "alkylsulfonyl" and "arylsulfonyl" as used herein denotes a group of formula —S(=O)$_2$R wherein R is alkyl or aryl respectively and alkyl and aryl are as defined herein.

The term "aryl" as used herein denotes an optionally substituted monocyclic or polycyclic-aromatic group comprising carbon and hydrogen atoms. Examples of suitable aryl groups include, but are not limited to, phenyl and naphthyl (e.g. 1-naphthyl or 2-naphthyl). Suitable substituents for aryl are selected from the group consisting of alkyl, alkenyl, alkynyl, aryloxy, cycloalkyl, acyl, acylamino, alkoxy, amino, alkylamino, dialkylamino, halogen, haloalkyl, hydroxy, nitro and cyano.

The term "acyl" ("alkylcarbonyl") as used herein denotes a group of formula C(=O)R wherein R is hydrogen, unbranched or branched alkyl containing 1 to 7 carbon atoms or a phenyl group.

The terms "alkoxycarbonyl" and "aryloxycarbonyl" as used herein denotes a group of formula —C(=O)OR wherein R is alkyl or aryl respectively and alkyl and aryl are as defined herein.

The term halogen stands for fluorine, chlorine, bromine or iodine, preferably fluorine, chlorine, bromine.

The term "acylating agent" as used herein refers to either an anhydride, acyl halide or other activated derivative of a carboxylic acid. The term "anhydride" as used herein refers to compounds of the general structure RC(O)—O—C(O)R wherein is as defined in the previous paragraph. The term "acyl halide" as used herein refers to the to group RC(O)X wherein X is bromo or chloro. The term "activated derivative" of a compound as used herein refers to a transient reactive form of the original compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to react with another reagent. In the context of the present invention activation of the carboxy group is of particular importance. The term acylating agent as used herein further includes reagents that produce carbonates esters OC(=O)OR$^4$ wherein R$^4$ is as defined hereinabove.

The term "protecting group" as used herein means a chemical group that (a) preserves a reactive group from participating in an undesirable chemical reaction; and (b) can be easily removed after protection of the reactive group is no longer required. For example, the trialkylsilyl is a protecting group for a primary hydroxyl function and an acetonide is a protecting group for a vicinal diol.

In the pictorial representation of the compounds given throughout this application, a thickened tapered wedge bond indicates a substituent which is above the plane of the ring to which the asymmetric carbon belongs (also designated β) and a dotted wedge bond indicates a substituent which is below the plane of the ring to which the asymmetric carbon belongs (also designated α).

The term "combination" or "combination therapy" as used herein in reference in administering a plurality of drugs in a therapeutic regimen by concurrent or sequential administration of the drugs at the same time or at different times.

The term "chemically-derivatized interferon" as used herein refers to an interferon molecule covalently linked to a polymer which alters the physical and/or pharmacokinetic properties of the interferon. A non-limiting list of such polymers include polyalkylene oxide homopolymers such as polyethylene glycol (PEG) or polypropylene glycol (PPG), polyoxyethylenated polyols, copolymers thereof and block copolymers thereof, provided that the water solubility of the block copolymers is to maintained. One skilled in the art will be aware of numerous approaches to linking the polymer and interferon (for example, see A. Kozlowski and J. M. Harris *J. Control. Release* 2001 72(1-3):217-24). A non-limiting list of chemically derivatized IFNα contemplated in the present patent includes peginterferon-α-2a (PEGASYS®) and peginterferon-α-2b (PEGINTRON®).

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—)

and amidine (—C(=NR)—NH— ⇌ —C(—NHR)=N—) tautomers. The latter two are particularly common in heteroaryl and heterocyclic rings and the present invention encompasses all tautomeric forms of the compounds.

Commonly used abbreviations include: acetyl (Ac), azo-bis-isobutyrylnitrile (AIBN), atmospheres (Atm), tert-butoxycarbonyl (Boc), di-tert-butyl pyrocarbonate or boc anhydride (BOC2O), benzyl (Bn), butyl (Bu), benzyloxycarbonyl (CBZ or Z), carbonyl diimidazole (CDI), 1,4-diazabicyclo[2.2.2]octane (DABCO), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propyl-ethylamine (DIPEA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et2O), O-(7-Azabenzotriazole-1-yl)-N,N,N'N'-tetramethyluronium hexafluorophosphate acetic acid (HATU), (HOAc), 1-N-hydroxybenzotriazole (HOBt), to high pressure liquid chromatography (HPLC), lithium hexamethyl disilazane (LiHMDS), methanol (MeOH), melting point (mp), MeSO2- (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-BuMe2Si (TBDMS), triethylamine (TEA or Et3N), 2,2,6,6-tetramethylpiperidine 1-oxyl (TEMPO), triflate or CF3SO2- (Tf), trifluoroacetic acid (TFA), thin layer chromatography (TLC), tetrahydrofuran (THF), trimethylsilyl or Me3Si (TMS), p-toluenesulfonic acid monohydrate (TsOH or pTsOH), 4-Me-C6H4SO2- or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, Nomenclature in Organic Chemistry, IUPAC 1979 Pergamon Press, Oxford.).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2$^{nd}$ edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

While chemical modification of the 2' and 3'-positions of nucleosides has been explored, modification of the 4'-position has been less prevalent, most like due to the added synthetic challenges associated with their synthesis. Maag et al. (Anti-HIV Activity of 4'-Azido and 4'-Methoxynucleosides, J. Med. Chem. 1992 35:1440-1451) disclose the synthesis of 4'-azido-2-deoxyribonucleosides and 4-azido nucleosides. C. O'Yang, et al. (Tetrahedron Lett. 1992 33(1):37-40 and 33(1): 41-44) disclose the synthesis 4'-cyano, 4'-hydroxymethyl- and 4'-formyl nucleoside compounds substituted nucleosides. These compounds were evaluated as anti-HIV compounds. Maag et al. (supra) taught 4'-azido nucleosides 16c can be prepared by addition of iodine azide to 5-methylene-tetrahydro-furan-2-yl nucleosides 15 wherein B is thymine, uracil, adenine or guanosine. In U.S.

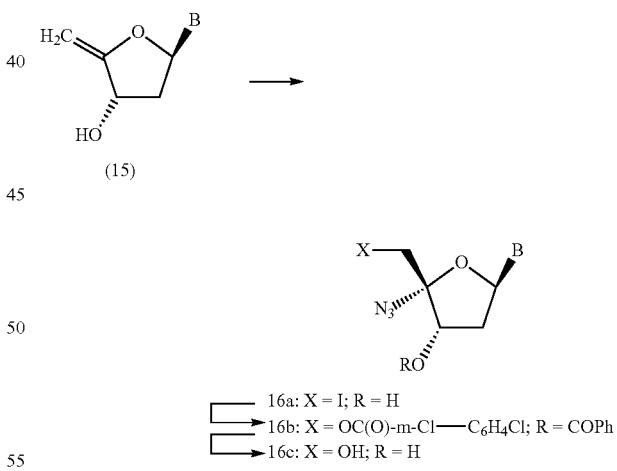

Patent Pub. No. 20050038240, published Feb. 17, 2005, T. J. Connolly et al., disclose an improved process for preparing 4'-azido nucleosides. In WO 02/100415, R. Devos et al. disclose the new 4'-substituted nucleoside derivatives which inhibit HCV NS5B viral DNA polymerase. The addition of iodine azide is most efficiently carried out on the uridines 15 (B=uracil) which can be converted to corresponding cytidine utilizing the method described by A. D. Borthwick et al., (J. Med. Chem. 1990 33(1):179; see also K. J. Divakar and C. B. Reese J. Chem. Soc., Perkin Trans. I 1982 1171-1176).

SCHEME A

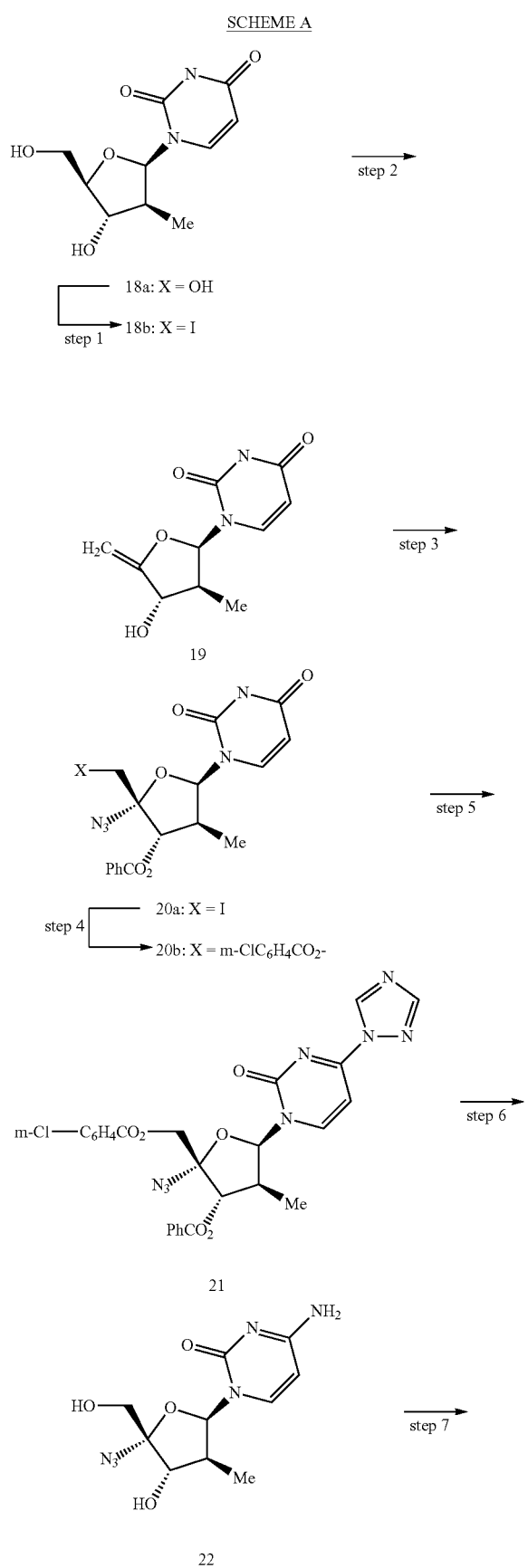

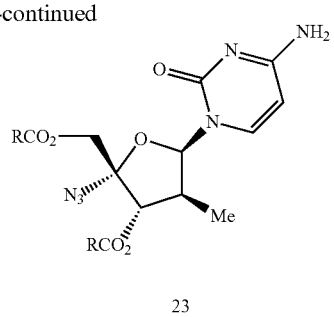

4-Amino-1-(5-azido-4-hydroxy-5-hydroxymethyl-3-methyl-tetrahydro-furan-2-yl)-1H-pyrimidin-2-one (22) is prepared from 1-(4-hydroxy-5-hydroxymethyl-3-methyl-tetrahydro-furan-2-yl)-1H-pyrimidine-2,4-dione (18a) (D. O. Cicero et al., "Stereoselective synthesis of novel analogs of 2'-deoxy- and 2',3'-dideoxynucleosides with potential antiviral activity", Bioorg. Med. Chem. Lett. 1994 4(7):861-6; A. Iribarren, EP547008 A1 entitled "Preparation of new (2'R)— and (2'S)-2'-deoxy-2'-C-hydrocarbyl antisense oligonucleotides useful in scientific research, therapeutics and diagnostics", published Jun. 16, 1993) using the procedure of Maag et al. (vide supra) (SCHEME A).

4-Amino-1-(5-azido-4-hydroxy-5-hydroxymethyl-3-methyl-tetrahydro-furan-2-yl)-1H-pyrimidin-2-one (22) exhibits good activity in a cell based replicon assay for HCV polymerase activity (TABLE I). Furthermore the compound exhibited low levels of cytoxicity in the assay.

TABLE I

| Compound | Maximum % Inhibition HCV Pol (100 µM) | Maximum % Cytotoxicity (100 µM) |
|---|---|---|
| 22 | 98.58 | 9.48 |

Nucleoside derivatives often are potent anti-viral (e.g., HIV, HCV, Herpes simplex, CMV) and anti-cancer chemotherapeutic agents. Unfortunately their practical to utility is often limited by two factors. Firstly, poor pharmacokinetic properties frequently limit the absorption of the nucleoside from the gut and the intracellular concentration of the nucleoside derivatives and, secondly, suboptimal physical properties restrict formulation options which could be employed to enhance delivery of the active ingredient.

Albert introduced the term prodrug to describe a compound which lacks intrinsic biological activity but which is capable of metabolic transformation to the active drug substance (A. Albert, Selective Toxicity, Chapman and Hall, London, 1951). Prodrugs have been recently reviewed (P. Ettmayer et al., J. Med. Chem. 2004 47(10):2393-2404; K. Beaumont et al., Curr. Drug Metab. 2003 4:461-485; H. Bundgaard, Design of Prodrugs: Bioreversible derivatives for various functional groups and chemical entities in Design of Prodrugs, H. Bundgaard (ed) Elsevier Science Publishers, Amersterdam 1985; G. M. Pauletti et al. Adv. Drug Deliv. Rev. 1997 27:235-256; R. J. Jones and N. Bischofberger, Antiviral Res. 1995 27; 1-15 and C. R. Wagner et al., Med. Res. Rev. 2000 20:417-45). While the metabolic transformation can catalyzed by specific enzymes, often hydrolases, the active compound can also be regenerated by non-specific chemical processes.

Pharmaceutically acceptable prodrugs refer to a compound that is metabolized, for example hydrolyzed or oxidized, in the host to form the compound of the present invention. The bioconversion should avoid formation fragments with toxicological liabilities. Typical examples of prodrugs include compounds that have biologically labile protecting groups linked to a functional moiety of the active compound. Alkylation, acylation or other lipophilic modification of the hydroxy group(s) on the sugar moiety have been utilized in the design of pronucleotides. These pronucleotides can be hydrolyzed or dealkylated in vivo to generate the active compound.

Factors limiting oral bioavailability frequently are absorption from the gastrointestinal tract and first-pass excretion by the gut wall and the liver. Optimization of transcellular absorption through the GI tract requires a $D_{(7.4)}$ greater than zero. Optimization of the distribution coefficient does not, however, insure success. The prodrug may have to avoid active efflux transporters in the enterocyte. Intracellular metabolism in the enterocyte can result in passive transport or active transport of the metabolite by efflux pumps back into the gut lumen. The prodrug must also resist undesired biotransformations in the blood before reaching the target cells or receptors.

While putative prodrugs can sometimes be rationally designed based on the chemical functionality present in the molecule, chemical modification of an active compound produces an entirely new molecular entity which can exhibit undesirable physical, chemical and biological properties absent in the parent compound. Regulatory requirements for identification of metabolites may pose challenges if multiple pathways lead to a plurality of metabolites. Thus, the identification of prodrugs remains an uncertain and challenging exercise. Moreover, evaluating pharmacokinetic properties of potential prodrugs is a challenging and costly endeavor. Pharmacokinetic results from animal models may be difficult to extrapolate to humans.

In U.S. Pat. No. 6,846,810 granted Jan. 25, 2005, J. A. Martin et al. have shown that acylated 4'-azidonucleosides have been found to be effective prodrugs. Di-acyl derivatives 23 of 22 can be prepared by acylation of the parent nucleoside 22.

The compounds of the present invention are conveniently prepared in one step by acylation of 22 in an aqueous organic solvent. The solvent can either be a homogenous aqueous solution or a two-phase solution. The pH of the aqueous organic solvent is maintained above 7.5 by addition of base to neutralize acid produced by the acylation. The base can be either an alkali or alkaline metal hydroxide or a tertiary amine. The reaction is carried out in the presence of DMAP which is known in the art to be a catalyst for acylation. An advantage of the present process is the desired product can be obtained without acylation of the heterocyclic base.

Alternately, the acylation is conveniently carried out with a corresponding acyl halide or anhydride in a solvent such as DCM, chloroform, carbon tetrachloride, ether, THF, dioxane, benzene, toluene, MeCN, DMF, sodium hydroxide solution or sulpholane optionally in the presence of an inorganic or organic base at temperatures between −20 to and 200° C., but preferably at temperatures between −10 and 160° C. The acylation reaction also may be carried out under Schotten Baumann in a biphasic organic-aqueous medium in the presence of phase-transfer catalysts and DMAP.

Selective acylation of the hydroxy groups can be accomplished. Alternatively the N-acyl group of an N,O,O-triacyl nucleoside can be selectively cleaved with zinc bromide to produce the protected diacyl compound (R. Kierzek et al. *Tetrahedron Lett.* 1981 22(38): 3762-64).

Selective acylation of the specific hydroxyl groups on the carbohydrate radical can be conveniently accomplished by enzyme catalyzed acylations or deacylations. Enzyme catalysis provides mild selective conditions for organic transformations. S. M. Roberts has reviewed preparative biotransformations (*J. Chem. Soc. Perkin* 1, 2001, 1475; 2000 611; 1999, 1; and, 1998 157). M. Mahmoudian et al. (*Biotechnol. Appl. Biochem.* 1999 29:229-233) reported the selective acylation of the 5'-position of 2-amino-9-β-D-arabinfuranosyl-6-methoxy-9H-purine with Novozyme 435, an immobilized preparation of *Candida antarctica* lipase. Other enzymes reported to selectively acylate the 5'-hydroxyl include: *Bacillus licheniformis* protease, Lipozyme IM (*Mucor miehei* lipase, CLEC-BL (*B. licheniformis* protease), savinase (*Bacillus* sp. protease), Novozyme-243 (*Bacillus licheniformis* protease), *Alcaligenes* sp. lipase and lipolase (Novo).

Lipolase® enzyme preparation (lipase from *Thermomyces lanuginosus*, Sigma catalog #L 0777) was found to selectively hydrolyze the 5'-acyl group of triacyl derivatives to afford 2',3'-diacyl compounds. In WO2004043894, G. G. Heraldsson et al. disclose the use of *T. lanuginosus* lipase for esterification of marine oils. N. Weber et al. (*Eur. J. of Lipid Sci. and Technol.* 2003 105(10):624-626) disclose *T. lanuginosus* catalyzed transesterification of methyl oleate. V. Bodai et al. (*Adv. Synth. Cat.* 2003 345(6 and 7):811-818) describe novel hydrolases from thermophilic filamentous fungi which can be used for selective biotransformations.

Other reports of regioselective enzymatic ester hydrolysis include: R. Hanson et al., *Bioorg. and Med. Chem.* 2000, 2681-2687 (synthesis of a lobucavir prodrug via regioselective acylation and hydrolysis); R. Pfau et al., *Syn Lett* 1999, 1817-1819 (selective hydrolysis of carbohydrate ester); A. Bianco et al, *J. of Mol. Cat. B: Enzymatic* 1997 209-212 (regioselective acylation and hydrolysis for synthesis of sialic acid derivatives); Y. Ota et. al., Bioscience, Biotechnology, Biochemistry (1997), 166-167 (regioselective ester hydrolysis of 1,2,3-trihexanolylglycerol); U. T. Bornscheuer et al., Enzyme Microbial Technol. 1995, 578-86 (lipase catalyzed syntheses of monoacylglycerol; review); C. T. Goodhue et al. WO9403625 (regioselective process for resolution of carbohydrate monoesters); N. W. Boaz, WO9115470 (Separation of alcohol-ester mixture by selective enzymatic hydrolysis); Y. S. Sanghvi et al. US2002142307 (regioselective hydrolysis of 3',5'-di-O-levulinylnucleosides); J. Garcia et al. *J. Org. Chem.* 2002, 4513-4519 (regioselective hydrolysis of 3',5'-di-O-levulinylnucleosides); O. Kirk et al. *Biocat and Biotransformation* (1995) 91-7 (lipase catalyzed regioselective acylation and deacylation of glucose derivatives).

One skilled in the art will recognize that the selective esterifications can also be accomplished by standard chemical methodology. Selective protection of the 5'-hydroxyl group has been described which will allow direct esterification of the 2'-hydroxyl or alternatively incorporation of a second protecting group which will allow deprotection and selective acylation of the primary alcohol.

The compounds of the present invention may be formulated in a wide variety of oral administration dosage forms and carriers. Oral administration can be in the form of tablets, coated tablets, hard and soft gelatine capsules, solutions, emulsions, syrups, or suspensions. Compounds of the present invention are efficacious when administered by suppository administration, among other routes of administration. The most convenient manner of administration is generally oral using a convenient daily dosing regimen which can be adjusted according to the severity of the disease and the patient's response to the antiviral medication.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage to range to be employed. The pharmaceutical compositions may be employed as solids, such as tablets or filled capsules, semisolids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound as used herein means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like. It should be understood that all references to pharmaceutically acceptable salts include solvent addition for Solid form preparations include powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

Suitable formulations along with pharmaceutical carriers, diluents and to excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (e.g., salt formulation), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.1 and about 10 g per day should be appropriate in monotherapy and/or in combination therapy. A preferred daily dosage is between about 0.5 and about 7.5 g per day, more preferred 1.5 and about 6.0 g per day. Generally, treatment is initiated with a large initial "loading dose" to rapidly reduce or eliminate the virus following by a decreasing the dose to a level sufficient to prevent resurgence of the infection. One of ordinary skill in treating diseases described herein will be able, without undue experimentation and in reliance on personal knowledge, experience and the disclosures of this application, to ascertain a therapeutically effective amount of the compounds of the present invention for a given disease and patient.

Therapeutic efficacy can be ascertained from tests of liver function including, but not limited to protein levels such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, to but not limited to, carbohydrate metabolism, amino acid and ammonia metabolism. Alternatively the therapeutic effectiveness may be monitored by measuring HCV-RNA. The results of these tests will allow the dose to be optimized.

In embodiments of the invention, the active compound or a salt can be administered in combination with another antiviral agent such as ribavirin, another nucleoside HCV polymerase inhibitor, a HCV non-nucleoside polymerase inhibitor, a HCV protease inhibitor, a HCV helicase inhibitor or a HCV fusion inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

Example 1 step 1—A solution of 18a (2.17 g, 8.96 mmol, 1 equiv.), imidazole (732 mg, 10.7 mmol, 1.2 equiv.) and $Ph_3P$ (2.82 g, 10.7 mmol, 1.2 equiv.) in dry THF (30 mL) was cooled on an ice-water bath, and a solution of iodine (2.50 g, 9.85 mmol, 1.1 equiv.) in dry THF (10 mL) was added dropwise over 10 min. The reaction mixture was stirred at 0-5° C. for another 10 min. The ice-water bath was removed and the reaction mixture was stirred at RT for 70 h. The reaction mixture was diluted with DCM (200 mL) and washed with 0.5 M $Na_2S_2O_3$ in saturated aqueous $NaHCO_3$ (150 mL). The aqueous layer was washed with DCM (4×50 mL). The combined organic extracts were dried ($Na_2SO_4$), filtered and concentrated. The residue was purified by $SiO_2$ chromatography to eluting with a MeOH/DCM stepwise gradient (1-5% v/v MeOH) to afford 1.75 g (55%) of 18b: $^1$H-NMR data ($CDCl_3$, 25° C.): δ 8.22 (br s, 1H), 7.59 (d, 1H), 6.19 (d, 1H), 5.75 (dd, 1H), 3.79 (m, 1H), 3.65 (m, 1H), 3.57 (dd, 1H), 3.47 (dd, 1H), 2.69 (m, 1H), 2.13 (d, 1H), 1.00 (d, 3H).

step 2—A solution of 18b (1.84 g, 5.22 mmol) and 0.4 M sodium methoxide in MeOH (81 mL) was stirred at 60° C. for 5 h, and was then cooled on an ice-water bath.

The pyridinium form DOWEX $H^+$ (prepared by treating DOWEX $H^+$ with pyridine (10 mL/g resin), filtering and washing with MeOH prior to use) was added portionwise until the pH of the solution was neutral (total 5-6 g). The ice-water bath was removed and the mixture was stirred at RT for 5 min. The resin was removed by filtration and washed with MeOH (100 mL). The residue was slurried in 6% EtOH/DCM and applied to a $SiO_2$ column and eluted with an EtOH/DCM gradient (6-7% v/v EtOH) to afford 0.942 g (80%) of 19 sufficiently pure for use in the next step.

step 3—Benzyltriethylammonium chloride (1.91 g, 8.4 mmol, 2 equiv.) and sodium azide (546 mg, 8.4 mmol, 2 equiv.) were suspended in dry MeCN (32 mL) and ultrasonisized for a few min. The resulting fine suspension was stirred at RT for 3 h, and then filtered under a $N_2$ atmosphere into a dry THF solution (30 mL) of compound 19 (942 mg, 4.2 mmol, 1 equiv.). NMM (140 µl, 0.106 mmol, 0.3 equiv.) was added and the resulting solution was cooled on an ice-water bath, and a solution of iodine (1.81 g, 7.14 mmol, 1.7 equiv.) in dry THF (39 mL) was added dropwise over 1 h. The resulting reaction mixture was stirred at 0-5° C. for another 2 h. N-Acetyl-L-cysteine (69 mg, 0.035 mmol, 0.1 equiv.) was added and the solution was stirred until the bubbling subsided. NMM (2.31 ml, 21.0 mmol, 5 equiv.) and DMAP (513 mg, 4.2 mmol, 1 equiv.) were added followed by a dropwise addition of benzoyl chloride (1.1 mL, 9.24 mmol, 2.2 equiv.). The reaction mixture was stirred at 0-5° C. for 30 min then stored in refrigerator overnight. Both TLC and LC-MS analysis showed a complete reaction. MeOH (5 mL) was added and after a few minutes the solvent was concentrated to half volume on rotavapor and then a solution of 0.1 M $Na_2S_2O_3$ in saturated aqueous $NaHCO_3$ (300 mL) was added under stirring, and the mixture was warmed to RT. The mixture was extracted with DCM (150 mL) and the aqueous layer was twice extracted with DCM (50 mL). The combined organic extracts were dried ($Na_2SO_4$), filtered and concentrated. The organic phase was then extracted with 5% citric acid and the aqueous phase was washed twice with DCM (2×50 ml). The DCM extracts were dried (Na2SO4), filtered and concentrated in vacuo. The residue was purified by $SiO_2$ chromatography eluting with a stepwise EtOH/DCM gradient (0, 0.5, 0.75, 1.0, 1.5 and 2.0% EtOH) to afford 1.72 g (83%) of 20a: $^1$H-NMR data ($CDCl_3$, 25° C.): δ 8.22-7.46 (7H), 6.49-6.39 (1H), 5.84 (dd, 1H), 5.55-5.47 (1H), 3.85 (d, 1H), 3.74 (d, 1H), 3.18 (m, 1H), 1.09 (d, 3H).

step 4—A solution of compound 20a (1.72 g, 3.47 mmol, 1 equiv.) in DCM (155 mL) was combined with a mixture of $Bu_4N HSO_4$ (825 mg, 2.43 mmol, 0.7 equiv.) and m-chlorobenzoic acid (359 mg, 2.29 mmol, 0.66 equiv.) in 1.75 M aqueous $K_2HPO_4$ (55 mL). The two-phase system was stirred vigorously at RT and two portions of a commercially available reagent mixture containing 55% MCPBA, 10% m-chlorobenzoic acid and 35% $H_2O$ (2×3.57 g, corresponding to 2×16.5 mmol or 2×3.28 equiv. MCPBA and 2×3.3 mmol or 2×0.66 equiv. m-chlorobenzoic acid) was added over a 1.5 h interval. The mixture was stirred vigorously at RT for another 18 h. LC-MS analysis showed >96% reaction. A solution of $Na_2S_2O_3.5H_2O$ (35 g) in saturated aqueous $NaHCO_3$ (500 mL) was added and the mixture was stirred vigorously at RT for 30 min. The organic layer was separated and the water layer was washed with DCM (2×10 mL). The combined organic layers were washed with saturated aqueous $NaHCO_3$ (40 mL). The aqueous $NaHCO_3$ layer was washed with DCM (2×10 mL). The combined organic layers were dried ($Na_2SO_4$), filtered and concentrated. The residue was purified by $SiO_2$ chromatography eluting with a EtOH/DCM gradient (1-2% v/v EtOH) to afford 1 g (56%) of 20b: $^1$H-NMR ($CDCl_3$, 25° C.): δ 8.19 (br s, 1H), 8.07-7.88 (4H), 7.65-7.36 (6H), 6.57-6.45 (1H), 5.64 (dd, 1H), 5.51-5.42 (1H), 4.80 (m, 2H), 3.24 (m, 1H), 1.09 (d, 3H).

step 5—The diester 20b (100 mg, 0.19 mmol, 1 equiv.) and 1,2,4-triazole (131 mg, 1.9 mmol, 10 equiv.) were co-evaporated from dry pyridine and redissolved in dry pyridine (1 mL). The solution was cooled in an ice-water bath, and a solution of POCl$_3$ (44 µl, 0.475 mmol, 2.5 equiv.) in MeCN (0.5 mL) was added dropwise over a few min. The reaction mixture was stirred at 0-5° C. for another 5 min, and then stirred at RT for 3 h. The reaction mixture was concentrated to half volume on rotary evaporator and then treated with saturated NH$_3$ in ethanol (20 mL) and the resulting solution was stirred at RT overnight. The residue after evaporation was purified by SiO$_2$ chromatography eluting with a stepwise EtOH/DCM gradient (6, 10, 15 and 20% v/v EtOH) to afford 0.036 g (66%) of 22 which was 98% pure on LCMS (~2.0% of contaminant 2'-α isomer). This reaction was repeated with 900 mg of compound 20b, resulting in 270 mg (54%, 97% pure) of 22 after chromatography: $^1$H-NMR (DMSO-d$_6$, 25° C.): δ 7.69 (d, 1H), 7.14 (d, 2H), 6.32 (br s, 1H), 5.72 (d, 1H), 5.78 (br s, 2H), 3.89 (br s, 1H), 3.74 (d,d,d, 2H), 2.54 (m, 1H), 0.77 (d, 3H).

Example 2

Isobutyric Acid (2R,3S,4S,5R)-5-(4-amino-2-oxo-2H-pyrimidin-1-yl)-2-isobutyryloxymethyl-4-methyl-tetrahydro-furan-3-yl Ester (25)

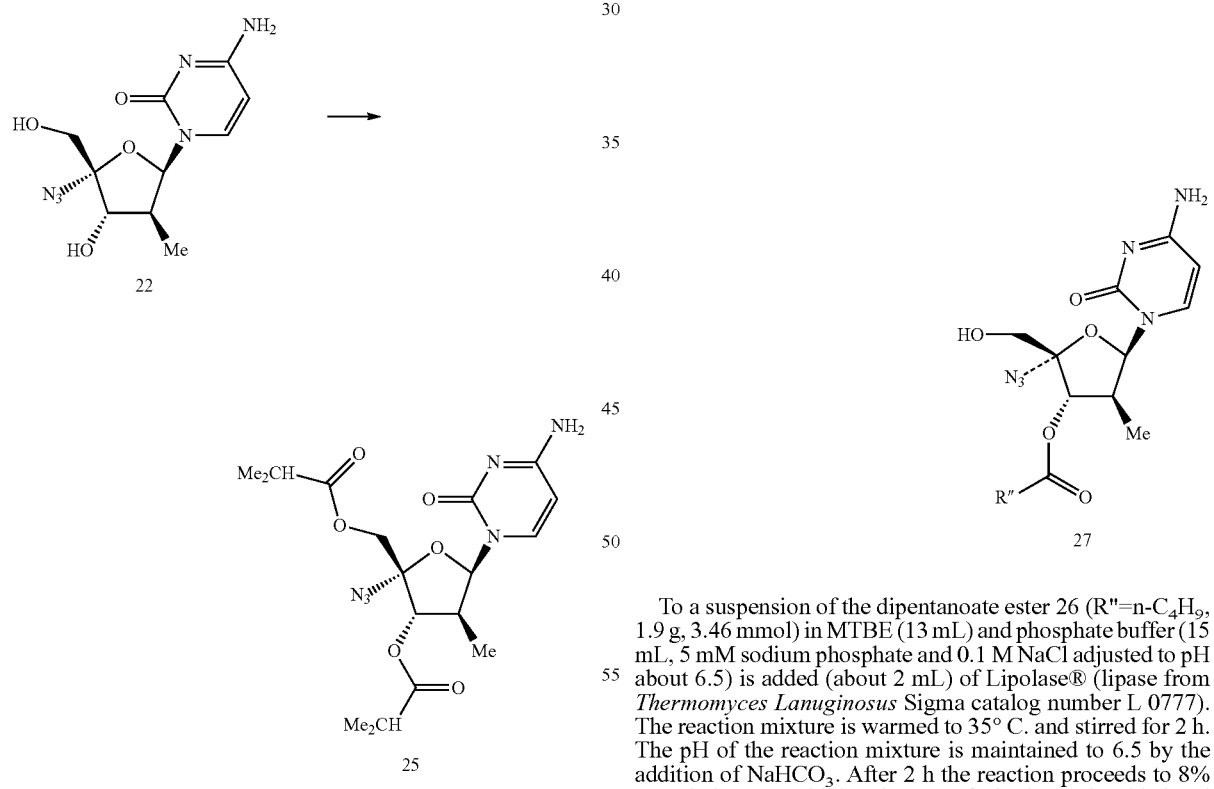

The pH of a solution of 22 (0.700 g, 2.48 mmol) in THF (7 mL) and diluted brine (7 mL) is adjusted with dilute aqueous KOH to ca. 11. Isobutyryl chloride (1.0 g) is added slowly (dropwise) to the ice-cold stirred biphasic reaction mixture while the pH is maintained pH at about 11 by adding dilute aqueous KOH as required. The extent of the reaction is monitored by HPLC. Added additional 1 eq. of isobutyryl chloride under the HPLC indicates near complete conversion. The reaction mixture is allowed to stand overnight at RT. The solution is diluted with EtOAc (50 mL) and the pH of the aqueous phase is adjusted to ca. 7.5 with conc. HCl. The phases are separated and the organic phase is washed three times with water and is evaporated to dryness to obtain 25.

Example 3

Pentanoic Acid (2R,3S,4S,5R)-5-(4-amino-2-oxo-2H-pyrimidin-1-yl)-2-azido-4-hydroxy-2-hydroxymethyl-tetrahydro-furan-3-yl Ester (27)

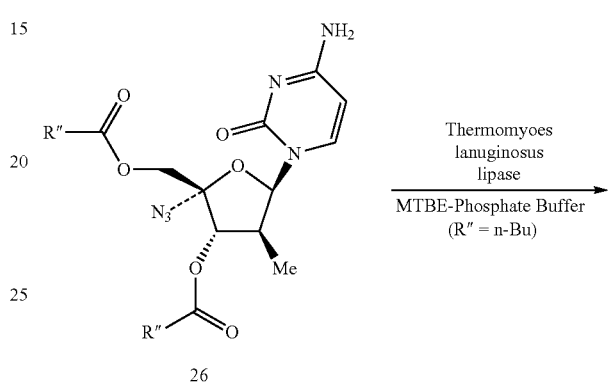

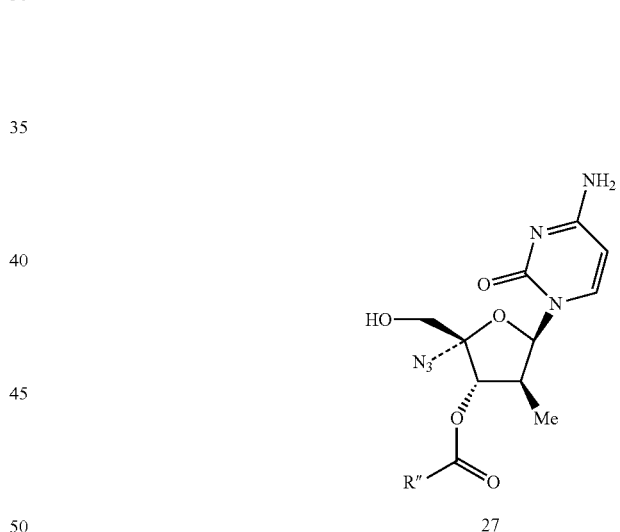

To a suspension of the dipentanoate ester 26 (R"=n-C$_4$H$_9$, 1.9 g, 3.46 mmol) in MTBE (13 mL) and phosphate buffer (15 mL, 5 mM sodium phosphate and 0.1 M NaCl adjusted to pH about 6.5) is added (about 2 mL) of Lipolase® (lipase from *Thermomyces Lanuginosus* Sigma catalog number L 0777). The reaction mixture is warmed to 35° C. and stirred for 2 h. The pH of the reaction mixture is maintained to 6.5 by the addition of NaHCO$_3$. After 2 h the reaction proceeds to 8% completion. An additional 2 mL of Lipolase® is added and stirring is continued for 6 h whereupon an additional 2 mL aliquot of the enzyme is added and the reaction is stirred for an additional 24 h. To the solution is added acetone (10 mL), MTBE (20 mL) and brine (10 mL) and the reaction is warmed to 50° C. The phases are separated and the organic phase is twice extracted with warm MTBE. The combined organic phases are twice washed with hot brine, are dried (Na$_2$SO$_4$), filtered and are concentrated in vacuo.

Example 4

Tetradecanoic Acid (2R,3S,4S,5R)-5-(4-amino-2-oxo-2H-pyrimidin-1-yl)-2-azido-3-butyryloxy-4-methyl-tetrahydro-furan-2-ylmethyl Ester (28)

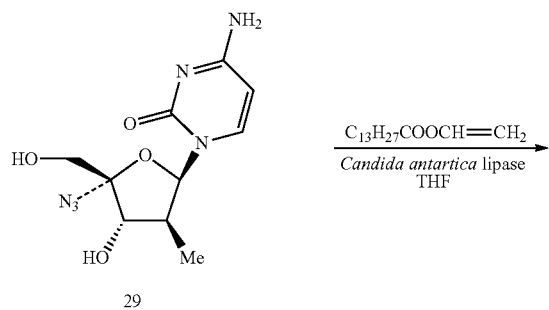

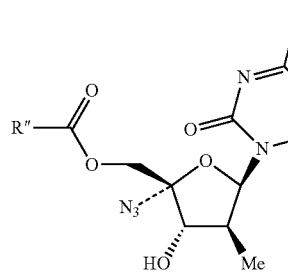

28: R″ = $C_{13}H_{27}$

A suspension of 29 (1.0 g, 3.52 mmol), vinyl myristate (1.2 g, 4.57 mmol), *Candida antartica* lipase immobilized on polyacrylate resin (0.30 g; Sigma catalog no. L4777 from Novosome) and THF (20 mL) is warmed to 60° C. overnight. HPLC analysis indicates that the reaction is about 33% complete and an additional 2.4 mL of vinyl myristate and 0.3 g of lipase is added. After an additional 48 h the reaction is 50% complete and an additional 0.3 g of the enzyme and 3 mL of vinyl myristate were added. After approximately 80 h (total reaction time) conversion to the monoester is complete. The crude reaction mixture is filtered through CELITE® and the filter pad washed with THF. The combined organic phase is evaporated. The residue is dissolved in MeOH (50 mL) and is extracted with hexane (2×20 mL). The methanolic solution is evaporated and the residue is dissolved in EtOAc and is washed with $NaHCO_3$ and the EtOAc phase is dried ($Na_2SO_4$) filtered and evaporated to afford a 0.930 g of 28 (R″=$C_{13}H_{27}$) which is purified by chromatography on $SiO_2$ eluting with a MeOH/DCM gradient (0 to 10% MeOH).

Example 5

3',5'-O-bis(L-valinyl)-4'-azido-2'-β-C-methyl-2'-deoxycytidine (34)

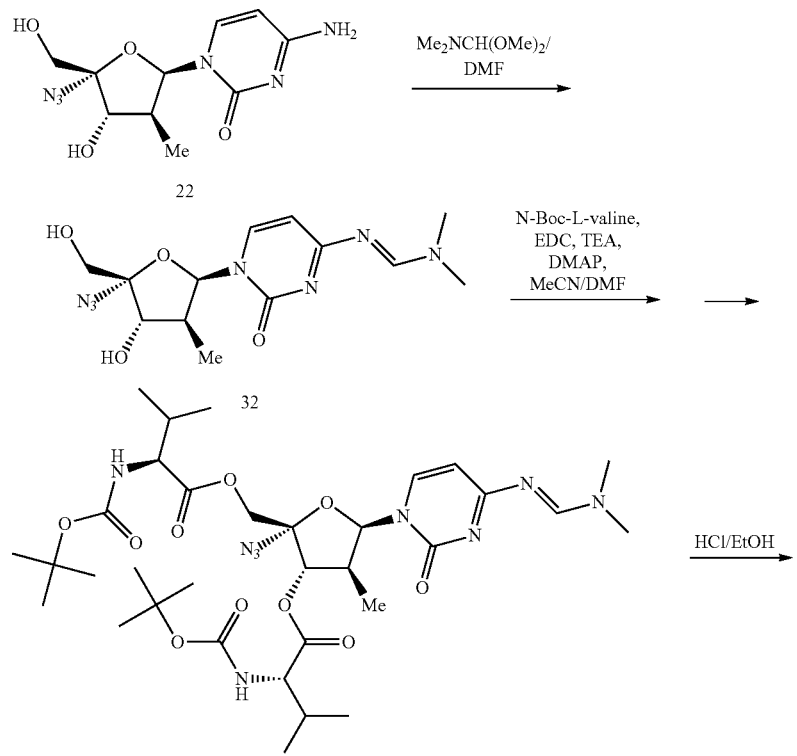

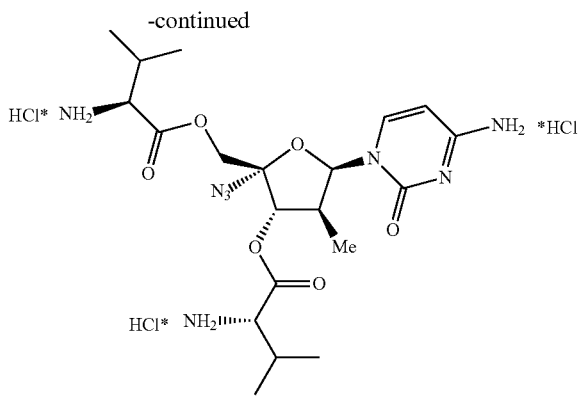

34

N⁴-[(Dimethylamino)methylene]-4'-azido-2'-β-C-methyl-2'-deoxycytidine (32)

A solution of 22 (1.81 g, 6.42 mmol) in DMF (30 ml) is treated with dimethylformamide dimethylacetal (8.2 mL, 61.73 mmol) and stirred for 1.5 h at room temperature. The solution is evaporated under reduced pressure and coevaporated with ethanol. Crystallization from ethanol/ether yields title compound 32.

3',5'-O-bis[N-(tert-Butoxycarbonyl)-L-valinyl]-N⁴-[(dimethylamino)methylene]-4'-azido-2'-β-C-methyl-2'-deoxycytidine (33)

To a solution of 32 (1.26 g, 3.74 mmol) in a mixture of dry acetonitrile (30 ml) to and DMF (15 ml) is successively added Boc-Val-OH (1.62 g, 7.48 mmol), EDC (1.43 g, 7.48 mmol), TEA (1.04 ml, 7.48 mmol) and DMAP (0.1 g). The resulting mixture is stirred at room temperature. The progress of the reaction is followed by HPLC and the reaction mixture recharged with Boc-Val-OH (0.63 g), EDC (0.72 g), TEA (0.52 ml) and DMAP (0.05 g). After the starting material is totally consumed, the solvent is removed under reduced pressure. The residue is taken up in ethyl acetate and washed with water and brine. Purification by silica gel column chromatography (gradient 5-40% EtOAc in Hexane) gives title compound 33.

3',5'-O-bis(L-valinyl)-4'-azido-2'-β-C-methyl-2'-deoxycytidine (Trihydrochloride Salt, 34)

To a concentrated solution of 33 (1.6 g, 2.17 mmol) in EtOH is slowly added 13 ml of 1M HCl in EtOH. The reaction mixture is stirred for 4 h at room temperature and diluted with ether. The precipitate is filtered and washed with ether to give the title compound 34 as the trihydrochloride salt.

Example 6

Alternative preparation of 3',5'-O-bis(isobutyryl)-4'-azido-2'-β-C-methyl-2'-deoxycytidine. (Isobutyric acid (2R,3S,4S,5R)-2-(4-amino-2-oxo-2H-pyrimidine-1-yl)-2-isobutyryloxymethyl-4-methyl-tetrahydrofuran-3-yl ester) (25).

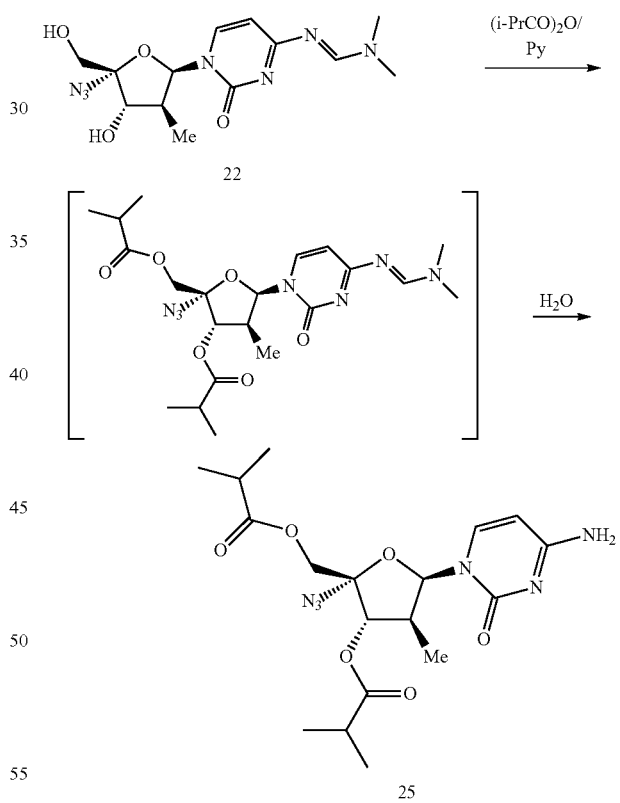

3',5'-O-bis(isobutyryl)-4'-azido-2'-β-C-methyl-2'-deoxycytidine (25)

To a solution of 22 (1.26 g, 3.74 mmol) in dry pyridine (25 ml) is added isobutyric anhydride (1.77 g, 11.2 mmol) at 0° C. The reaction is followed by HPLC and when completed quenched with water to destroy the excess of isobutyric anhydride and remove N⁴-protection. The solvents are evaporated at reduced pressure and coevaporated with ethanol. The residue is dissolved in ethyl acetate and washed with NaHCO₃, brine. Purification by silica gel column chromatography (gradient 10-40% EtOAc in hexane) gives title compound 25

Example 7
4'-Azido-3'-O-(L-valinyl)-2'-β-C-methyl-2'-deoxycytidine (37)
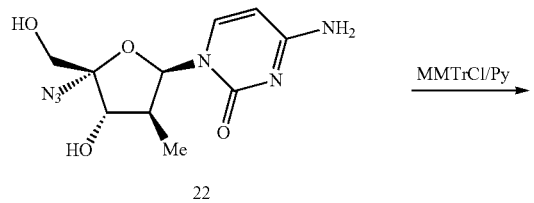
MMTrCl/Py →
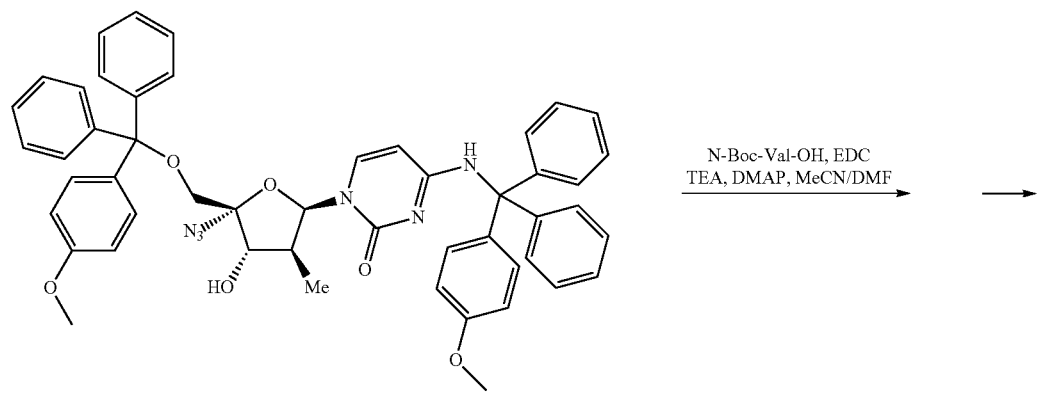
N-Boc-Val-OH, EDC
TEA, DMAP, MeCN/DMF →
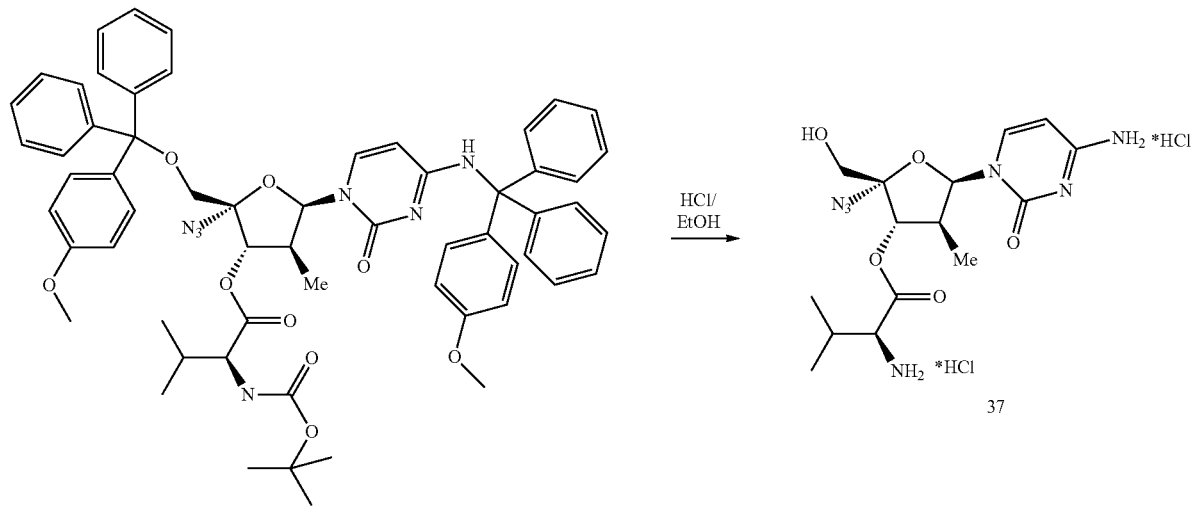

N⁴,5'-O-bis(monomethoxytrityl)-4'-azido-2'-β-C-methyl-2'-deoxycytidine (35)

A mixture of 22 (2.82 g, 10 mmol) and MMTrCl (9.15 g, 30 mmol) in pyridine (50 ml) is stirred overnight at 80° C. After addition of MeOH (5 ml) and stirring for another 2 h, the solvent is evaporated and the residue divided between ethyl acetate and water. The organic phase is washed with water, brine and evaporated. Purification by silica gel column chromatography (0-5% MeOH in DCM) gives title compound 35.

N⁴,5'-O-bis(monomethoxytrityl)-4'-azido-3'-[N-(tert-Butoxycarbonyl)-L-valinyl]-2'-β-C-methyl-2'-deoxycytidine (36)

To a solution of 35 (3.09 g, 3.74 mmol) in a mixture of dry acetonitrile (30 ml) and DMF (15 ml) are successively added Boc-Val-OH (0.81 g, 3.74 mmol), EDC (0.72 g, 3.74 mmol), TEA (0.52 ml, 3.74 mmol) and DMAP (0.07 g). The resulting mixture is stirred at room temperature. The progress of the reaction is followed by HPLC and the reaction mixture recharged with Boc-Val-OH (0.4 g), EDC (0.36 g), TEA (0.26 ml) and DMAP (0.04 g). When the starting material is totally consumed, the solvent is removed under reduced pressure. The residue is taken up in ethyl acetate and washed with water and brine. Purification by silica gel column chromatography (gradient 5-40% EtOAc in Hexane) gives title compound 36.

4'-Azido-3'-O-(L-valinyl)-2'-β-C-methyl-2'-deoxycytidine (dihydrochloride salt, 37)

To a concentrated solution of 36 (2.4 g, 2.34 mmol) in EtOH is slowly added 13 ml of 1M HCl in EtOH. The reaction mixture is stirred for 4 h at room temperature and diluted with ether. The precipitate is filtered and washed with ether to give the title compound (37) as the dihydrochloride salt.

Example 8

4'-Azido-3'-O-isobutyryl-2'-β-C-methyl-2'-deoxycytidine (38)

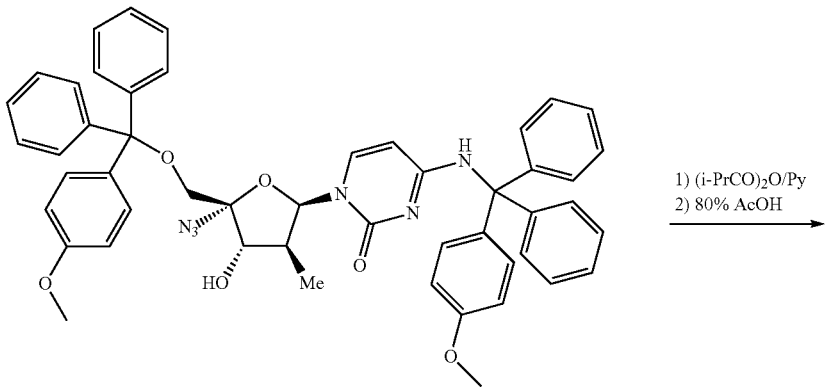

35

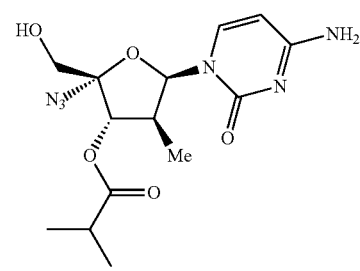

38

4'-Azido-3'-O-isobutyryl-2'-β-C-methyl-2'-deoxycytidine (38)

To a solution of 35 (3.09 g, 3.74 mmol) in dry pyridine (25 ml) is added isobutyric anhydride (0.89 g, 5.61 mmol) at 0° C. The reaction is followed by HPLC and when complete quenched with water to destroy the excess of isobutyric anhydride. The solvents are evaporated at reduced pressure and coevaporated with ethanol. The residue is dissolved in ethyl acetate, washed with NaHCO₃, brine and evaporated. The crude MMTr protected 3'-isobutyril derivative is dissolved in 80% AcOH and stirred at 50° C. until fully deprotected of MMTr groups. The solvent is evaporated and the residue was purified by silica gel column chromatography (0-20% MeOH in DCM) to give the title compound 38.

Example 9

5'-O-(L-valinyl)-4'-azido-2'-β-C-methyl-2'-deoxycytidine (43)

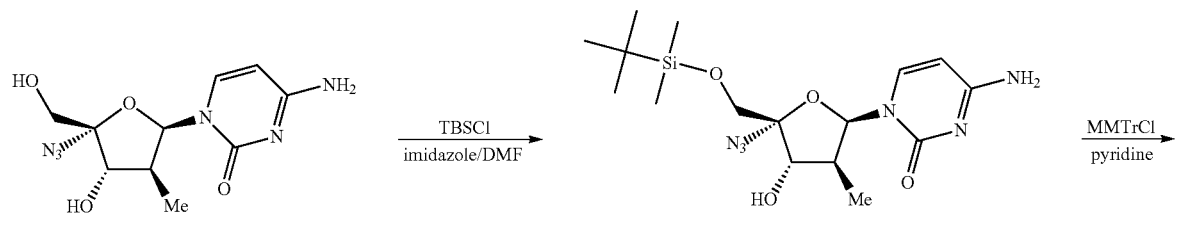

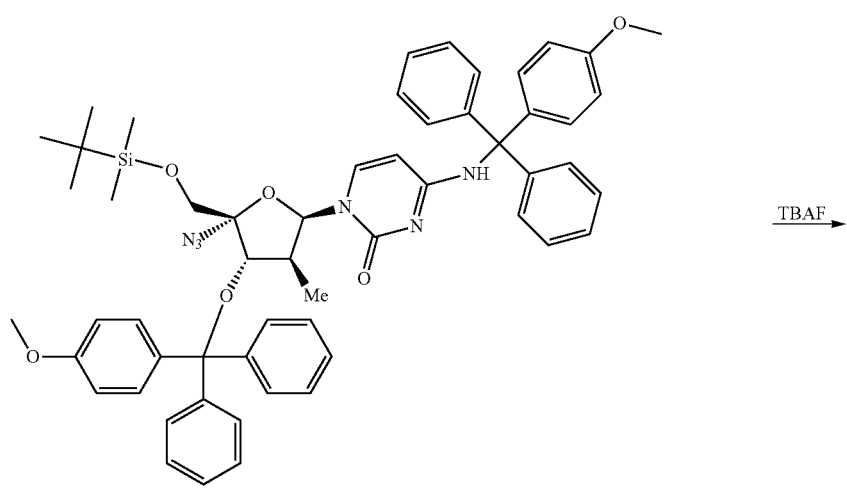

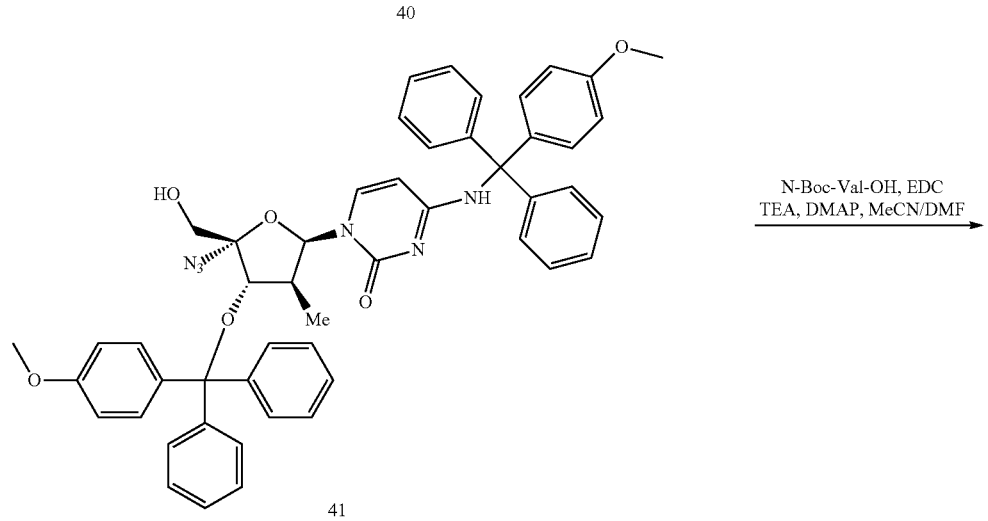

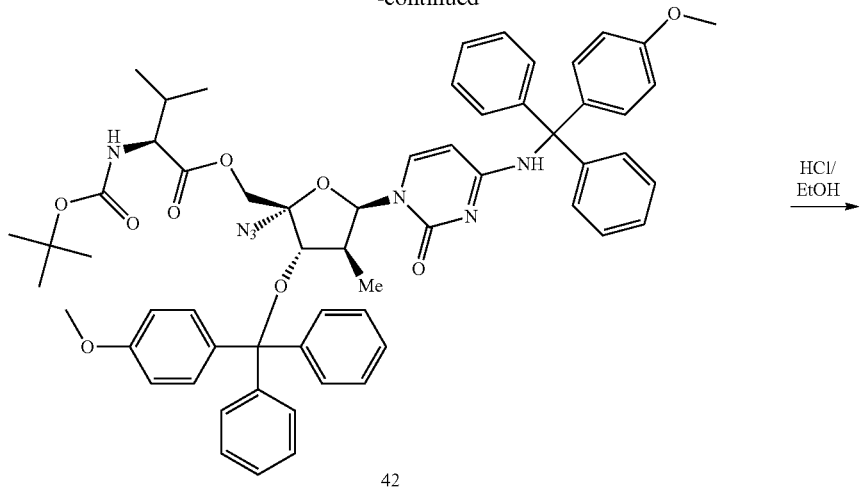

42

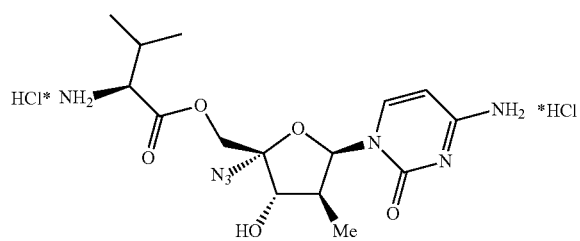

43

5'-O-t-Butyldimethylsilyl-4'-azido-2'-β-C-methyl-2'-deoxycytidine (39)

To a solution of 22 (2.82 g, 10 mmol) in DMF (5 ml) is added imidazole (1.02 g, 15 mmol) and TBSCl (1.95 g, 13 mmol). When the starting material is consumed the reaction mixture is quenched with MeOH (1 ml) and divided between ethyl acetate and water. The organic phase is washed with water, brine and evaporated. The residue is purified by silica gel column chromatography (0-20% MeOH in DCM) to give the title compound 39.

5'-O-t-Butyldimethylsilyl-4'-azido-$N^4$,3'-O-bis(monomethoxytrityl)-2'-β-C-methyl-2'-deoxycytidine (40)

A mixture of 39 (3.7 g, 9.34 mmol) and MMTrCl (8.63 g, 28 mmol) in dry pyridine (50 ml) is stirred overnight at 80° C. After addition of MeOH (5 ml) and stirring for another 2 h, the solvent is evaporated and the residue divided between ethyl acetate and water. The organic phase is washed with water, brine and evaporated. Purification by silica gel column chromatography (0-5% MeOH in DCM) gives title compound 40.

4'-Azido-$N^4$,3'-O-bis(monomethoxytrityl)-2'-β-C-methyl-2'-deoxycytidine (41)

A solution of 40 (5.3 g, 5.64 mmol) in THF (20 ml) is treated with 1M TBAF in THF (5.7 ml, 5.7 mmol) and stirred for 2 h at room temperature. The reaction mixture is diluted with ethyl acetate, washed with water, brine and evaporated. Chromatography on silica gel (0-5% ethyl acetate in $CHCl_3$) gives the title compound 41.

5'-[N-(tert-Butoxycarbonyl)-L-valinyl]-$N^4$,3'-O-bis(monomethoxytrityl)-4'-azido-2'-β-C-methyl-2'-deoxycytidine (42)

To a solution of 41 (3.09 g, 3.74 mmol) in a mixture of dry acetonitrile (30 ml) to and DMF (15 ml) are successively added Boc-Val-OH (0.81 g, 3.74 mmol), EDC (0.72 g, 3.74 mmol), TEA (0.52 ml, 3.74 mmol) and DMAP (0.07 g). The resulting mixture is stirred at room temperature. The progress of the reaction is followed by HPLC and the reaction mixture recharged with Boc-Val-OH (0.4 g), EDC (0.36 g), TEA (0.26 ml) and DMAP (0.04 g). When the starting material is totally consumed, the solvent is removed under reduced pressure. The residue is taken up in ethyl acetate and washed with water and brine. Purification by silica gel column chromatography (gradient 5-40% EtOAc in Hexane) gives the title compound 42.

5'-O-(L-valinyl)-4'-azido-2'-β-C-methyl-2'-deoxycytidine (dihydrochloride salt, 43)

To a concentrated solution of 42 (2.4 g, 2.34 mmol) in EtOH is slowly added 13 ml of 1M HCl in EtOH. The reaction mixture is stirred for 4 h at room temperature and diluted with ether. The precipitate is filtered and washed with ether to give the title compound 43 as the dihydrochloride salt.

Example 10

5'-O-isobutyryl-4'-azido-2'-β-C-methyl-2'-deoxycytidine (44)

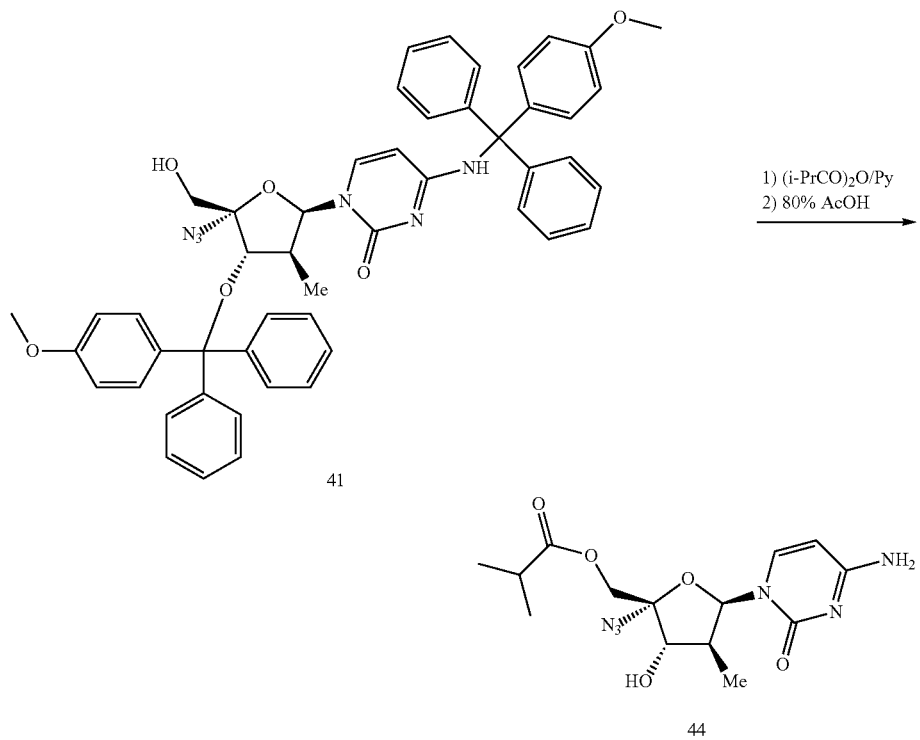

5'-O-isobutyryl-4'-azido-2'-β-C-methyl-2'-deoxycytidine (44)

To a solution of 41 (3.09 g, 3.74 mmol) in dry pyridine (25 ml) is added isobutyric anhydride (0.89 g, 5.61 mmol) at 0° C. The reaction is followed by HPLC and when completed quenched with water to destroy the excess of isobutyric anhydride. The solvents are evaporated at reduced pressure and coevaporated with ethanol. The residue is dissolved in ethyl acetate, washed with $NaHCO_3$, brine and evaporated. The crude MMTr protected 3'-isobutyryl derivative is dissolved in 80% AcOH and stirred at 50° C. to until fully deprotected of MMTr groups. The solvent is evaporated and the residue purified by silica gel column chromatography (0-20% MeOH in DCM) to give the title compound 44.

Example 11

Renilla Luciferase Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla* luciferase gene was introduced into the first open reading frame of a replicon construct NK5.1 (Krieger et al., *J. Virol.* 75:4614), immediately after the internal ribosome entry site (IRES) sequence, and fused with the neomycin phosphotransferase (NPTII) gene via a self-cleavage peptide 2A from foot and mouth disease virus (Ryan & Drew, EMBO Vol 13:928-933). After in vitro transcription the RNA was electroporated into human hepatoma Huh7 cells, and G418-resistant colonies were isolated and expanded. Stably selected cell line 2209-23 contain replicative HCV subgenomic RNA, and the activity of *Renilla* luciferase expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation.

*Renilla* luciferase HCV replicon cells (2209-23) cultured in Dulbecco's MEM (GibcoBRL cat no. 31966-021) with 5% fetal calf serum (FCS, GibcoBRL cat. no. 10106-169) were plated onto a 96-well plate at 5000 cells per well, and incubated overnight. Twenty-four hours later, different dilutions of chemical compounds in the growth medium were added to the cells, which were then further incubated at 37° C. for to three days. At the end of the incubation time, the cells in white plates were harvested and luciferase activity was measured by using Dual-Luciferase reporter assay system (Promega cat no. E1960) All the reagents described in the following paragraph were included in the manufacturer's kit, and the manufacturer's instructions were followed for preparations of the reagents. The cells were washed twice with 200 µl of phosphate buffered saline (pH 7.0) (PBS) per well and lysed with 25 µl of 1× passive lysis buffer prior to incubation at room temperature for 20 min. One hundred microliter of LAR II reagent was added to each well. The plate was then inserted into the LB 96V microplate luminometer (MicroLumatPlus, Berthold), and 100 µl of Stop & Glo® reagent was injected into each well and the signal measured using a 2-second delay, 10-second measurement program. $IC_{50}$, the concentration of the drug required for reducing replicon level by 50% in relation to the untreated cell control value, can be calculated from the plot of percentage reduction of the luciferase activity vs. drug concentration.

WST-1 reagent from Roche Diagnostic (cat no. 1644807) was used for the cytotoxicity assay. Ten microliter of WST-1 reagent was added to each well including wells that contain media alone as blanks. Cells were then incubated for 1 to 1.5 hours at 37° C., and the OD value was measured by a 96-well plate reader at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration.

Example 12

MT4/XTT Assay

Compounds of the invention can also be assayed for activity against concomitant infections. For example, individuals at risk for blood transmitted infections such as HCV are sometimes co-infected with HIV.

Compounds can be assayed for HIV activity, for example using multiple determinations with XTT in MT-4 cells (Weislow et al, J Nat Cancer Inst 1989, vol 81 no 8,577 et seq), preferably including determinations in the presence of 40-50% human serum to indicate the contribution of protein binding. In short a typical XTT assay uses human T cell line MT4 cells grown in RPMI 1640 medium supplemented with 10% fetal calf serum (or 40-50% human serum as appropriate), penicillin and streptomycin seeded to into 96 well microplates ($2 \cdot 10^4$ cells/well) infected with 10-20 $TCID_{50}$ per well of HIV-1$_{IIIB}$ (wild type) or mutant virus, such as those bearing RT Ile 100, Cys 181 or Asn 103 mutations. Serially diluted test compounds are added to respective wells and the culture incubated at 37° C. in a $CO_2$ enriched atmosphere and the viability of cells is determined at day five or six with XTT vital dye. Results are typically presented as $ED_{50}$ μM. The compound of Example 1 displays an $ED_{50}$ of around 0.6 μM in an XTT assay.

Example 13

Intracellular Triphosphate Concentration & Half Life

The putative active species of the compounds of the invention is β-D-2'-deoxy-2'-β-C-methyl-4'-azidocytidine triphosphate. The stability of the triphosphate is determined in fresh human primary hepatocytes (CellzDirect or In Vitro Technologies) pre-incubated with tritiated parent compound. The hepatocytes are cultured on 6 well collagen coated plates (BD Biosciences), typically at 1.5 million cells/well using complete serum-containing medium (CellzDirect or In Vitro Technologies)/37° C./5% $CO_2$. Various hepatocyte strains are available, such as Hu497, MHL-091806 and Hu504 and it is therefore useful to test such strains in parallel and calculate mean values from a range of strains.

The pre-incubation is typically for 24 hours with 2 μM of the tritiated parent at 10 μC/ml. At $t_0$ the cell monolayer is washed with cell culture medium to remove extracellular parent compound and the cell cultures re-incubated with fresh cell culture medium. The concentration of intracellular triphosphate is quantified at different time points up to 72 hours. Convenient time points are 0, 0.5, 1, 2, 4, 6, 8, 24, 48 & 72 hours with duplicate cell cultures for each time point.

At the appropriate timepoint, cells are harvested by aspirating the cell culture medium and washing the cells with cold PBS. Cells are scraped into an extraction medium such as 1 ml pre-chilled 60% (v/v) methanol, extracted into methanol for 24 h at −20° C. Extracted samples are centrifuged to remove cell debris. The supernatant is removed to fresh tubes, evaporated and stored in liquid nitrogen for analysis. Dried pellets of cell extract are dissolved in water and nanofiltered (eg nanosep centrifugal device, Pall Life Sciences). Prior to HPLC analysis samples are spiked with unlabelled to reference standards for the parent and its monophosphate, diphosphate and triphosphate forms. A typical HPLC system employs an ion exchange HPLC with Whatman Partisil 10SAX (4.6×250 mm) column coupled to a radiometric detector (such as β-RAM, IN/US Systems Inc). A conventional mobile phase linear gradient 0% aqueous buffer to 100% phosphate buffer (eg 0.5M $KH_2PO_4$/0.8M KCl) at flow rates such as 1 ml/min. For detection of radiolabeled species in the β-RAM, a 5:1 ratio of FloScint IV or UltimaFloAP (Perkin Elmer) to column eluent can be used. The parent and intracellular metabolites are identified by comparison of the retention times of the intracellular species in the radiochromatogram with the retention of non-radioactive reference standards spiked in the cell extract samples and detected by UV absorption, typically at 270 nm.

The time course of uptake and phosphorylation is measured in an analogous fashion whereby human primary hepatocytes are incubated with tritiated compound of the invention, for example 2 μM and 10 μCi/ml. A suitable time course is addition to duplicate cultures of compound at 72, 48, 24, 16, 6 and 1 hour before cell harvesting. To determine the dose response of phosphorylation of the compounds of the invention, human primary hepatocytes are incubated with tritiated test compound, for example at 0, 2, 10, 25, 50, 100 and 250 μM for 24 hours. Final concentrations are achieved by supplementing with non-radiolabeled test compound. Duplicate cell cultures are harvested, generally after 24 hours incubation.

In such assays the mean triphosphate half-life of the compounds of the invention was 21.4 hours (standard deviation 4.22 hours). The steady state triphosphate level at 24 hours at 2 μM is around 15 μM/million cells. Using 3 μl as the average volume of human liver parenchymal cells, this concentration of triphosphate corresponds to a value substantially in excess of the Ki of the parent compound.

A long triphosphate half life and high concentration implies that antivirally active concentrations of the active species will be present in HCV infective cells for protracted time periods after dosing. This in turn means that minimum diurnal trough levels will remain high even with QD dosing, thereby minimizing opportunities for sub-optimal exposure to drug resulting in the development of drug escape mutants.

In contrast to the long triphosphate half life of the invention, the triphosphate half life of the analogous 2'-β-C methyl compound PSI-6130 (β-D-2'-deoxy-2'-fluoro-2'-β- to C-methylcytidine (depicted below) was only 4.7 hours, with a 24 hour steady state triphosphate concentration of only 1.3 pM/million cells.

Example 13

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 500 to 1000 mg each.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound having the formula:

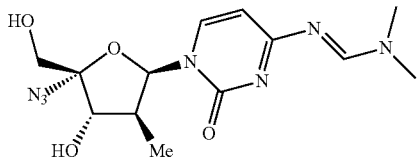

($N^4$-[(Dimethylamino)methylene]-4'-azido-2'-β-C-methyl-2'-deoxycytidine) or a pharmaceutically acceptable salt thereof.

2. A compound having the formula:

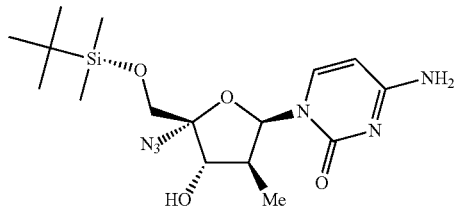

(5'-O-t-Butyldimethylsilyl-4'-azido-2'-β-C-methyl-2'-deoxycytidine) or a pharmaceutically acceptable salt thereof.

3. A method of treating an Hepatitis C viral (HCV) infection comprising administering to a patient in need thereof a therapeutically effective amount of a compound according to claim 1 or 2.

4. A pharmaceutical composition comprising a compound according to claim 1 or 2 admixed with at least one pharmaceutically acceptable carrier, diluent or excipient.

* * * * *